United States Patent
Larson et al.

(10) Patent No.: US 10,031,135 B2
(45) Date of Patent: *Jul. 24, 2018

(54) DETECTION OF BIOAGENTS USING A SHEAR HORIZONTAL SURFACE ACOUSTIC WAVE BIOSENSOR

(71) Applicants: STC.UNM, Albuquerque, NM (US); SANDIA CORPORATION, Albuquerque, NM (US)

(72) Inventors: Richard S. Larson, Albuquerque, NM (US); Brian Hjelle, Placitas, NM (US); Pam R. Hall, Albuquerque, NM (US); David C. Brown, Albuquerque, NM (US); Marco Bisoffi, Albuquerque, NM (US); Susan M. Brozik, Albuquerque, NM (US); Darren W. Branch, Albuquerque, NM (US); Thayne L. Edwards, Albuquerque, NM (US); David Wheeler, Albuquerque, NM (US)

(73) Assignees: STC.UNM, Albuquerque, NM (US); SANDIA CORPORATION, Albuquerque, NM (US)

(*) Notice: Subject to any disclaimer, the term of this patent is extended or adjusted under 35 U.S.C. 154(b) by 38 days.

This patent is subject to a terminal disclaimer.

(21) Appl. No.: 14/172,429

(22) Filed: Feb. 4, 2014

(65) Prior Publication Data
US 2014/0249042 A1 Sep. 4, 2014

Related U.S. Application Data

(62) Division of application No. 12/069,284, filed on Feb. 8, 2008, now Pat. No. 8,709,791.

(Continued)

(51) Int. Cl.
*G01N 33/543* (2006.01)
*C12Q 1/6825* (2018.01)

(52) U.S. Cl.
CPC ..... G01N 33/54373 (2013.01); C12Q 1/6825 (2013.01)

(58) Field of Classification Search
CPC ........................ G01N 33/54373; C12Q 1/6825
See application file for complete search history.

(56) References Cited

U.S. PATENT DOCUMENTS

| 5,658,732 A | 8/1997 | Ebersole et al. |
| 8,709,791 B2 | 4/2014 | Larson et al. |

(Continued)

OTHER PUBLICATIONS

Alf ME, et al. Chemical Vapor Deposition of Conformal, Functional, and Responsive Polymer Films. Materials Views, 2010;22:1993-2027.

(Continued)

*Primary Examiner* — Melanie Y Brown
(74) *Attorney, Agent, or Firm* — Henry D. Coleman; R. Neil Sudol

(57) ABSTRACT

Viruses and other bioagents are of high medical and biodefense concern and their detection at concentrations well below the threshold necessary to cause health hazards continues to be a challenge with respect to sensitivity, specificity, and selectivity. Ideally, assays for accurate and real time detection of viral agents and other bioagents would not necessitate any pre-processing of the analyte, which would make them applicable for example to bodily fluids (blood, sputum) and man-made as well as naturally occurring bodies of water (pools, rivers). We describe herein a robust biosensor that combines the sensitivity of surface acoustic waves (SAW) generated at a frequency of 325 MHz with the specificity provided by antibodies and other ligands for the detection of viral agents. In preferred embodiments, a (Continued)

lithium tantalate based SAW transducer with silicon dioxide waveguide sensor platform featuring three test and one reference delay lines was used to adsorb antibodies directed against Coxsackie virus B4 or the negative-stranded category A bioagent Sin Nombre virus (SNV), a member of the genus Hantavirus, family Bunyaviridae, negative-stranded RNA viruses. Rapid detection (within seconds) of increasing concentrations of viral particles was linear over a range of order of magnitude for both viruses, although the sensor was approximately $50\times10^4$-fold more sensitive for the detection of SNV. For both pathogens, the sensor's selectivity for its target was not compromised by the presence of confounding Herpes Simplex virus type 1. The biosensor was able to detect SNV at doses lower than the load of virus typically found in a human patient suffering from hantavirus cardiopulmonary syndrome (HCPS). Further, in a proof-of-principle real world application, the SAW biosensor was capable of selectively detecting SNV agents in complex solutions, such as naturally occurring bodies of water (river, sewage effluent) without analyte pre-processing.

15 Claims, 7 Drawing Sheets

Related U.S. Application Data

(60) Provisional application No. 60/900,416, filed on Feb. 9, 2007, provisional application No. 60/926,827, filed on Apr. 30, 2007, provisional application No. 61/009,656, filed on Dec. 31, 2007.

(56) References Cited

U.S. PATENT DOCUMENTS

| | | | | |
|---|---|---|---|---|
| 2002/0187464 | A1* | 12/2002 | Klempner | G01N 33/56983 506/6 |
| 2003/0085397 | A1 | 5/2003 | Greens et al. | |
| 2003/0196477 | A1 | 10/2003 | Auner et al. | |
| 2004/0005582 | A1 | 1/2004 | Shipwash | |
| 2004/0072208 | A1* | 4/2004 | Warthoe | C12Q 1/6825 435/6.11 |
| 2006/0029929 | A1 | 2/2006 | Hunt et al. | |
| 2006/0213271 | A1 | 9/2006 | Edmonson et al. | |
| 2008/0138797 | A1* | 6/2008 | Hunt | B82Y 5/00 435/6.16 |
| 2008/0186477 | A1 | 8/2008 | Wang et al. | |

OTHER PUBLICATIONS

Barie N, et al. Vacuum-deposited wave-guiding layers on STW resonators based on LiTaO3 substrate as love wave sensors for chemical and biochemical sensing in liquids. Ultrasonics, 2010;50:606-612.

Harding GL, et al. Design and properties of quartz-based Love wave acoustic sensors incorporating silicon dioxide and PMMA guiding layers. Smart Mater Struct, 1997;7:716-720.

Herrmann F, et al. Sensors Based on Shear-Horizontal Surface Acoustic Waves in Layered Quartz/Sio2 and LiTaO3/Si)2 Structures. IEEE Ultrasonics Symposium, 1999;413-416.

Martin F, et al. Pulse mode shear horizontal-surface acoustic wave (SH-SAW) system for liquid based sensing applications. Biosensors and Bioelectronics, 2004;19:627-632.

Nakamura H, et al. Suppression of Transverse-Mode Spurious Responses for SAW Resonators on SiO2/Al/LiNbO3 Structure by Selective Removal of SiO2. IEEE Transactions of Ultrasonics, Ferroelectrics, and Frequency Control, 2011;58:2188-2193.

Winkler A, et al. SAW-grade SiO2 for advanced microfluidic devices. Proc SPIE, 2009;7362, 73621Q, doi: 10.1117/12.822290.

Branch DW, et al. Love Wave Acoustic Array Biosensor Platform for Autonomous Detection. IEEE Ultrasonics Symposium, 2007;260-263.

Berkenpas E, et al. Detection of *Escherichia coli* O157:H7 with langasite pure shear horizontal surface acoustic wave sensors. Biosensors and Bioelectronics, 2006;21:2255-2262.

Branch DW, Brozik S. Low-Level Detection of a Bacillus Anthracis Simulant Using Love-Wave Biosensors on 36 degree YX LiTa03. Microsensor Science and Technology Department, Sandia National Laboratories, Albuquerque, NM. Mar. 2003, p. 1-33.

Bronze MS, et al. Viral Agents as Biological Weapons and Agents of Bioterrorism. Am J Med Sci, 2002;323 (6):316-325.

Deisingh AK, Thompson M. Biosensors for the detection of bacteria. Can J Microbiol, 2004;50:69-77.

Frydenberg A, Starr M. Hand, foot, and mouth disease. Australian Family Physician, 2003;32(8):594-595.

Hjelle B. Vaccines against hantaviruses. Expert Rev Vaccines, 2002;1(3):373-384.

Jay M, et al. Seroepidemiologic Studies of Hantavirus Infection Among Wild Rodents in California. Emerging Infectious Diseases, 1997;3(2):183-190.

Mertz GJ, et al. Diagnosis and treatment of new world hantavirus infections. Curr Opin Infect Dis, 2006;19:437-442.

Moll N, et al. A Love wave immunosensor for whole *E. coli* bacteria detection using an innovative two-step immobilization approach. Biosensors and Bioelectronics, 2007;22:2145-2150.

Palacios G, Oberste MS. Enteroviruses as agents of emerging infectious diseases. Journal of NeuroVirology, 2005;11:424-433.

Tam PE. Coxsackievirus Myocarditis: Interplay between Virus and Host in the Pathogenesis of Heart Disease. Viral Immunology, 2006;19(2):133-146.

Tamarin O, et al. Real time device for biosensing: design of a bacteriophage model using love acoustic waves. Biosensors and Bioelectronics, 2003;18:755-763.

Tassew N, Thompson M. Binding affinity and inhibitory potency of neomycin and streptomycin on the Tat peptide interaction with HIV-1 TAR RNA detected by on-line acoustic wave sensor. Org Biomol Chem, 2003;1:3268-3270.

Velappan N, et al. Selection and characterization of scFv antibodies against the Sin Nombre hantavirus nucleocapsid protein. Journal of Immunological Methods, 2007;321:60-69.

Xiao R, et al. Sin Nombre Viral RNA Load in Patients with Hantavirus Cardiopulmonary Syndrome. The Journal of Infectious Diseases, 2006;194:1403-1409.

Josse et al.; Guided Shear Horizontal Surface Acoustic Wave Sensors for Chemical and Biochemical Detection in Liquids; 2001; Analytical Chemistry, vol. 73 pp. 5937-5944.

Bisoffi M. et al.; Detection of viral bioagents using a shear horizontal surface acoustic wave biosensor; Biosensors and Bioelectronics 2008, vol. 23, pp. 1397-1403.

Bisoffi, Marco et al.; Rapid Detection of Human Immunodeficiency Virus Types 1 and 2 by Use of an Improved Piezoelectric Biosensor 2013; vol. 56, pp. 1685-1691. first published Mar. 20, 2013.

* cited by examiner

DETECTION OF BIOAGENTS USING A SHEAR HORIZONTAL SURFACE ACOUSTIC WAVE BIOSENSOR

RELATED APPLICATIONS

The present application is a continuation of and claims priority from U.S. patent application Ser. No. 12/069,284, filed Feb. 8, 2008, now U.S. Pat. No. 8,709,791, which claims the benefit of priority of U.S. provisional application Ser. No. 60/900,416, filed Feb. 9, 2007, Ser. No. 60/926,827, filed Apr. 30, 2007 and Ser. No. 61/009,656, filed Dec. 31, 2007, each of which applications is incorporated by reference in its entirety herein.

GRANT SUPPORT

This work was conducted with support from the National Science Foundation, grant number IIS-0434120, and from the National Institute of Allergy and Infectious Diseases, grant numbers UO1 AI56618 and UO1 AI054779, and from the U.S. Department of Energy to Sandia Corporation, grant number DE-AC04-94AL85000.

FIELD OF THE INVENTION

The present invention relates to the use of a shear horizontal surface acoustic wave biosensor adapted to detect a large number of biological or chemical agents, including viruses, virus fractions (membranes, biomarkers, etc.) and other microbes (prions, eukaryotic and prokaryotic cells, including fungus and bacteria) amino acid based biological agents including polypeptides, DNA and RNA, lipids (including glycosylated, phosphorylated, acetylated lipids) and synthetic chemicals, including nerve gas and other chemical agents. In the present invention, a piezoelectric material, in particular, a lithium tantalate ($LiTaO_3$) wafer is modified to provide on its surface at least one ligand and preferably, a plurality of ligands, which bind to one or more biological agents to be detected by the biosensor. In the present invention, a biosensor to which is bound a free (unbound) ligand, emits a characteristic wave which can be readily measured- and if the ligand becomes bound to a biological agent, the ligand-biological agent will produce a modified wave pattern which can be measured and result in the qualitative identification (including, in certain aspects, quantitative or concentration information) of the biological agent in a sample. The method and apparatus are adaptable to identify a large number of biological agents as otherwise described in detail herein.

BACKGROUND OF THE INVENTION

Recently, there has been a heightened interest in developing rapid and reliable methods of detection of microorganisms involved in bioterrorism, food poisoning, and clinical problems. Biosensors are devices under intense development to achieve these goals and a number of different types of transduction modes are currently investigated, including electrochemical, optical, thermal, and acoustic (Deisingh, 2004). Shear horizontal surface acoustic wave (SH-SAW) devices that are based on horizontally polarized surface shear waves (HPSSW) enable label-free, sensitive and cost-effective detection of biomolecules in real time and have been used for the detection of bacteria and viral DNA (Berkenpas et al., 2006; Branch and Brozik, 2004; Moll et al., 2007). A SAW device typically has a planar electrode structure consisting of a piezoelectric substrate containing inter-digital transducers (IDTs) (Branch and Brozik, 2004). An often used substrate compound that meets many of the required conditions for successful HPSSW generation is lithium tantalate ($LiTaO_3$) (Branch and Brozik, 2004; Martin et al., 2004). Applying an alternating voltage via the IDTs at high frequency (typically from 80 to 400 MHz), HPSSW are generated on the substrate. These HPSSW result in a specific resonance frequency that is characteristic for the substrate surface wave velocity. The frequency is sensitive to measurable changes on the sensor surface, for example caused by specific biological interactions.

BRIEF DESCRIPTION OF THE INVENTION

The present invention is directed to a biological ligand based biosensor comprising a biological ligand which is complexed (coated or tethered) directly or indirectly to the surface of a piezoelectric material of a biosensor apparatus which is combined to accommodate surface acoustic wave (SAW) technology.

The biosensor of the present invention has, complexed on its surface, any number of biological ligands, which are capable of binding to bioagents which are to be identified. The biological ligands may be chosen for their ability to bind a specific bioagent, or alternatively, to bind to a group or class of bioagents, depending upon common features which exist between the biological ligand which is tethered to the surface of the biosensor apparatus and the bioagent to be identified. The biological ligand may be amino acid based, such as a polypeptide (including modified polypeptides such as glycosylated polypeptides, multimeric polypeptides, including polypeptides which are multimerized by cross-linking devices, nanoparticles, etc., and antibodies), nucleic acid based (single stranded DNA, single stranded RNA, oligonucleotides, including modified oligonucleotides) or lipid based (including glycosylated lipid). The biological ligand is chosen to be specific for a given bioagent such that when a bioagent comes in contact with the ligand, the SAW associated with the biosensor reflects a change indicative of the binding of the bioagent to the ligand.

The present invention is based upon a biosensor apparatus featuring surface chemistries which are capable of transducing shear horizontal surface acoustic waves (SH-SAW) generated by piezoelectric materials, in particular, lithium tantalate ($LiTaO_3$), when connected to an electrical circuit at defined frequencies. The technology is manufactured onto wafers that can be sectioned into functional units ("chips"). These units can be applied to a SAW detection board featuring a fluidic housing and a connection of the chip via aluminum delay lines to an output interface with a computing device (e.g., a laptop computer or other computing device) for measurements of SAW. The biosensor apparatus is depicted in FIGS. 1a-d.

In a method of the present invention, a sample is presented to the ligand based biosensor as described above and a determination of the existence (binding) of a bioagent in the sample which is made by determining a change in a surface acoustic wave emanating from the biosensor which evidences the binding of the bioagent to the ligand.

BRIEF DESCRIPTION OF THE DRAWINGS

FIG. 2 is a representative SAW biosensor plot showing the response to $1.8 \times 10^4$ SNV particles per µl. Output was captured using a custom LabVIEW (National Instruments; website ni.com) program. The data is reported as phase differential mass shift $\Delta\varphi$ (indicated by double-headed arrow) on the y-axis as a function of time on the x-axis, corresponding to the maximal difference between buffer-calibrated phase differential before addition of agent (arrow A at ~280 seconds) and after stabilization of signal (arrow B at ~420 seconds). Dotted lines indicate detection at ~15 seconds and maximal signal difference at ~2 minutes after addition of the agent. Single vertically oriented data points are visible as a function of time. See text for details.

DETAILED DESCRIPTION OF THE INVENTION

Figure 1A:
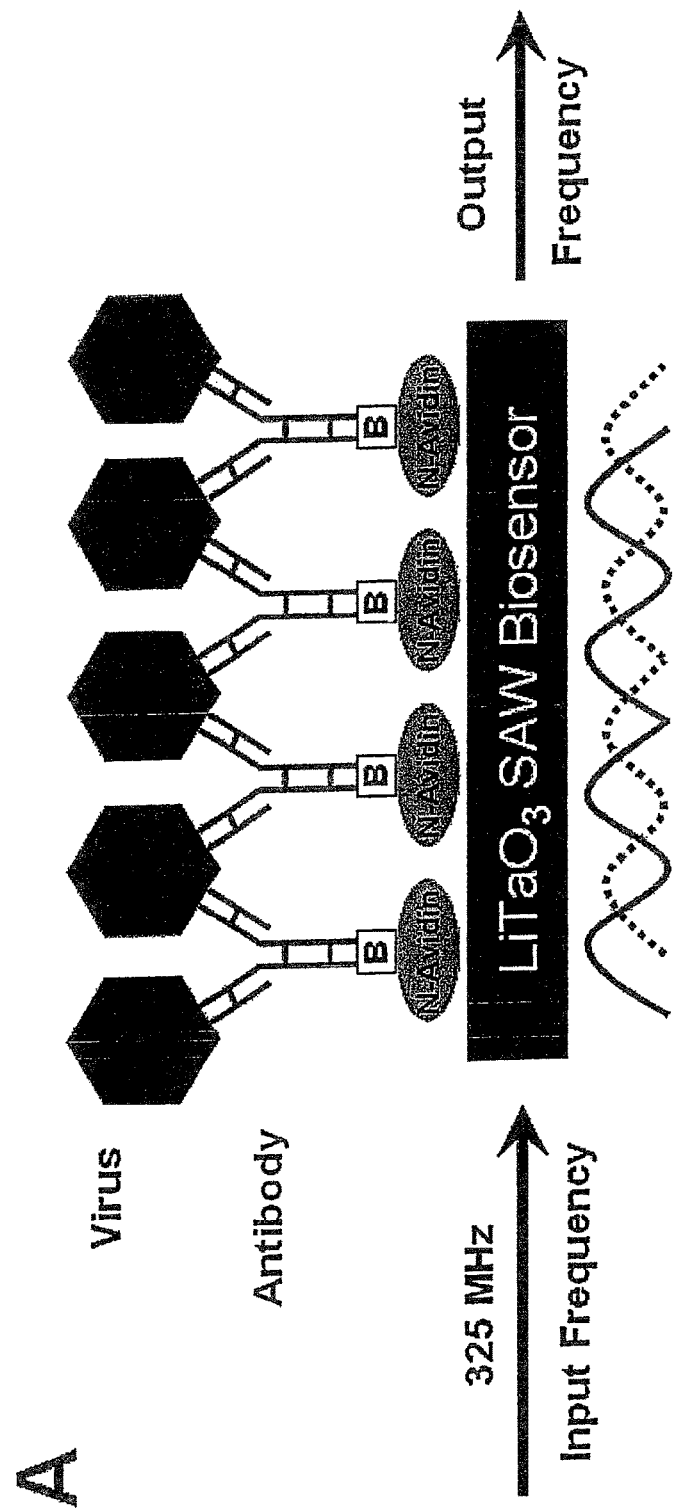
FIG. 1A is a diagram depicting an antibody based virus surface acoustic wave (SAW) biosensor in accordance with the present invention. The lithium tantalate ($LiTaO_3$) sensor surface was coated with NeutrAvidin Biotin Binding Protein (N-Avidin) and coupled to biotinylated [B] monoclonal anti-JVB antibody for Coxsackie virus. Anti-SNV-G1 glycoprotein scFv antibody for SNV detection was coupled directly. Molecular interaction between virus and antibody elicits an acoustic wave leading to a change in the input frequency of 325 MHz.

The following terms shall be used to describe the present invention. In instances where a term is not defined, then the term shall be given its ordinary meaning as understood by those of ordinary skill within the context of its use.

The term "effective" is used to describe, within context, an amount of a component or compound used in the present invention in a manner consistent with its intended use.

The term "ligand" or "capture molecule" shall mean a biological compound comprising amino acids, DNA or RNA (polynucleotides or oligonucleotides), lipids or carbohydrates which may be complexed (coated or tethered) onto the surface of a piezoelectric material in a biosensor apparatus according to the present invention. Amino acid based ligands include antibodies (monoclonal or polyclonal) and fragments thereof (e.g. single chain Fab antibody fragments), polypeptides (at least 25 mer), oligopeptides (about 3 mer to about 25 mer or more), peptide multimers (palindromes, crosslinked multilmeric peptides, nanoparticles, among others). DNA or RNA ligands are polynucleotides, oligonucleotides which may be single stranded DNA, single stranded RNA, oligonucleotides (phosphate backbone, etc.,) and lipids, including glycosylated lipids and carbohydrates, including complex carbohydrates. Although the most common type of capture molecule is an antibody, other peptides such as receptors, enzymes, other proteins, including dendrimers (especially in the case of prions), nucleotides (polynucleotides and oligonucleotides, aptamers, primarily DNA molecules, but also stable RNA (preferably, single stranded) molecules may be used. In addition, lipids and carbohydrates (chitosan, lectins, among others) may be used as capture molecules, depending upon the nature of the bioagent to be detected.

The ligand may be designed and used to detect primary amino acid sequences, especially including biomarkers on cell or particle surfaces (including mutations, translocations, truncations and isoforms), posttranslational modifications, phosphorylations, glycoslation, non-peptide organics (nerve gasses, alkylating agents, other organic toxins), lipids, including glycosylated, phosphorylated or acetylated lipids, double stranded DNA or RNA (especially after denaturing) and single stranded DNA or RNA. The ligand may include a nucleocapsin protein capture DNA, as well as other capture DNA and RNA molecules (such as aptamers), among others.

Ligands may be broadly used and applied. Essentially any biological molecule capable of binding a bioagent as otherwise described herein finds use in the present invention. Exemplary ligands may be found throughout the literature and are numerous. An excellent directory which provides a large number of amino acid based ligands, especially monoclonal and polyclonal antibodies for use in the present invention is Linscott's directory of immunological and biological reagents, available at linscottsdirectory.com. DNA and RNA ligands (e.g., capture DNA/RNA) which bind to bioagents may be found throughout the literature. In applications of the present invention, depending upon the type and actual size of the ligand to be tethered to the biosensor, the number/concentration of ligands which are tethered to a biosensor ranges from 1 to about 100,000 or more per $cm^2$, from 10 to about 50,000, about 50 to about 25,000, about 100 to about 20,000, about 500 to about 15,000 about 750 to about 12,500, about 1000 to about 10,000, about 1250 to about 7500, about Exemplary ligands include monoclonal and polyclonal antibodies, including anti-Coxsackie virus monoclonal antibody (mouse IgG2a), anti-Sin Nombre virus (SNV) G1 glycoprotein (single chain Fv, scFv from phage display), anti-Herpes Simplex virus I (HSV-1) antibody (polyclonal), anti-αvβ3 integrin antibody, anti-Interleukin-12 (IL-12)

monoclonal antibody (mouse IgG1), anti-Interleukin-6 (IL-6) polyclonal, among others; peptides, including 9 amino acid cyclic peptides from Sin Nombre Virus phage display as described in greater detail herein, 9 amino acid cyclic peptides from Andes virus phage display as described in greater detail herein, linear peptides including a 16 amino acid peptide from Dengue virus phage display; nucleic acids, including Sin Nombre virus-N(SNV-N) and SNV-M capture DNA (analyte is Sin Nomber virus (SNV) RNA) and BRCA1 capture DNA (single-stranded, 30 mer (base units in length)-analyte is BRCA1 DNA (single stranded-60 base units in length), among others.

The term "bioagents" or "analytes" used synonymously within context, shall mean viruses and their extracts, prions and their extracts, eurcaryotic cells, fragments and extracts, prokaryotic cells (especially bacteria), fragments and extracts, prokaryotic spores, fragments and extracts, protein and peptide markers (biomarkers, especially biomarkers on cell surfaces), serum proteins, isolated proteins, synthetic chemicals, viral membranes, eukaryotic membranes, eukaryotic cell parts, including mitochondria and other organelles, prokaryotic membranes, DNA viruses (single and double stranded DNA viruses), RNA viruses (single and double stranded RNA viruses), point mutations (any organism), single nucleotide polymorphism (any organism), mRNA's, rTNAs, micro RNAs (from any organism). In preferred aspects of the invention, the bioagent or analyte is a virus or extract, a prion or a DNA or RNA molecule. Any virus for which a monoclonal or polyclonal antibody may be raised, for which a binding polypeptide is available or for which a capture DNA is available are particularly preferred bioagents or analytes for use in the present invention.

Exemplary viruses which may be viral bioagents in the present invention include animal, plant, fungal and bacterial viruses. Viral biogents which may be detected by the biosensors according to the present invention include those which impact animals, especially mammals, in particular humans, domestic animals and include, for example, Papovaviruses, e.g. polyoma virus and SV40; Poxviruses, e.g. vaccinia virus and variola (smallpox); Adenoviruses, e.g., human adenovirus; Herpesviruses, e.g. Human Herpes Simplex types I and II; Parvoviruses, e.g. adeno associated virus (AAV); Reoviruses, e.g., rotavirus and reovirus of humans; Picornaviruses, e.g. poliovirus; Togaviruses, including the alpha viruses (group A), e.g. Sindbis virus and Semliki forest virus (SFV) and the flaviviruses (group B), e.g. dengue virus, yellow fever virus and the St. Louis encephalitis virus; Retroviruses, e.g. HIV I and II, Rous sarcoma virus (RSV), and mouse leukemia viruses; Rhabdoviruses, e.g. vesicular stomatitis virus (VSV) and rabies virus; Paramyxoviruses, e.g. mumps virus, measles virus\and Sendai virus; Arena viruses, e.g., lassa virus; Bunyaviruses, e.g., bunyawere (encephalitis); Coronaviruses, e.g. common cold, GI distress viruses, Orthomyxovirus, e.g., influenza; Caliciviruses, e.g., Norwak virus, Hepatitis E virus; Filoviruses, e.g., ebola virus and Marburg virus; and Astroviruses, e.g. astrovirus, among others.

Bioagents such as Sin Nombre virus, influenza (especially H5N1 influenza), Herpes Simplex Virus (HSV1 and HSV-2), Coxsackie virus, Human immunodeficiency virus (I and II), Andes virs, Dengue virus, Papilloma, Epstein-Barr virus (mononucleosis), Variola (smallpox) and other pox viruses, West Nile virus, influenza (H5N1) find use as bioagents in the present invention.

A short list of animal viruses may be relevant bioagent targets for use in the present invention:
Reovirus
Rotavirus
Enterovirus
Rhinovirus
Hepatovirus
Cardiovirus
Aphthovirus
Parechovirus
Erbovirus
Kobuvirus
Teschovirus
Norwalk virus
Hepatitis E virus
Rubella virus
Lymphocytic choriomeningitis virus
HIV-1, HIV-2,
HTLV-I
Herpes Simplex Virus 1 and 2
Sin Nombre Virus
Coxsackie Virus
Dengue virus
Yellow fever virus
Hepatitis A virus
Hepatitis B virus
Hepatitis C virus
Influenzavirus A, B and C
Isavirus,
Thogotovirus
Measles virus
Mumps virus
Respiratory syncytial virus
California encephalitis virus
Hantavirus
Rabies virus
Ebola virus
Marburg virus
Corona virus
Astrovirus
Borna disease virus
Variola (smallpox virus)

Plant viruses also are relevant bioagents for use in the present invention. The present invention may be used to detect plant viruses, especially in agricultural applications.

Plant viruses, which may serve as bioagents (analytes) for the present include the following:

Geminiviruses e.g., bigeminivirus, monogeminivirus and bybrigeminivirus; Partitiviruses, e.g., alphacryptoviruses and betacryptoviruses; Potyviruses, e.g., bymoviruses and ipomoviruses; Bromoviruses, e.g. cucumoviruses and bromoviruses; Comoviruses, e.g. fabiviruses, neopoviruses and comoviruses; Rhabodoviruses, e.g., cytorhabdoviruses, nucleorhabdoviruses; Reoviruses, e.g., oryzaviruses and phytoreoviruses; Satellite viruses, e.g., satelliviruses; Tombusviruses, e.g., carmoviruses; Sequiviruses,e.g., sequiviruses and waikaviruses; among numerous others (see below).

Plant Virus Genuses, include the following:
Alfamoviruses: Bromoviridae
Alphacryptoviruses: Partitiviridae
Badnaviruses
Betacryptoviruses: Partitiviridae
Bigeminiviruses: Geminiviridae
Bromoviruses: Bromoviridae
Bymoviruses: Potyviridae
Capilloviruses Carlaviruses
Carmoviruses: Tombusviridae
Cauliimoviruses
Closteroviruses
Comoviruses: Comoviridae
Cucumoviruses: Bromoviridae
Cytorhabdoviruses: Rhabdoviridae
Dianthoviruses
Enamoviruses
Fabaviruses: Comoviridae
Fijiviruses: Reoviridae
Furoviruses
Hordeiviruses
Hybrigeminiviruses: Geminiviridae
Idaeoviruses
Ilarviruses: Bromoviridae
Ipomoviruses: Potyviridae
Luteoviruses
Machlomoviruses
Macluraviruses
Marafiviruses
Monogeminiviruses: Geminiviridae
Nanaviruses
Necroviruses
Nepoviruses: Comoviridae
Nucleorhabdoviruses: Rhabdoviridae
Oryzaviruses: Reoviridae
Ourmiaviruses
Phytoreoviruses: Reoviridae
Potexviruses
Potyviruses: Potyviridae
Rymoviruses: Potyviridae
Satellite RNAs
Satelliviruses
Sequiviruses: Sequiviridae
Sobemoviruses
Tenuiviruses
Tobamoviruses
Tobraviruses
Tombusviruses: Tombusviridae
Tospoviruses: Bunyaviridae
Trichoviruses
Tymoviruses
Umbraviruses
Unassigned potyviruses: Potyviridae
Unassigned rhabdoviruses: Rhabdoviridae
Varicosaviruses
Waikaviruses: Sequiviridae
Ungrouped viruses A much more complete list of viral bioagents which may be analytes in the present invention include, for example, those which are listed at: Virus Taxonomy, the Sixth Report of the International Committee on Taxonomy of Viruses (ICTV) 1995 See, the corresponding website: tulane.edu/~dmsander/WWW/335/VirusList.html, which is referenced herein.

Prions are another class of important bioagents which may be detected using the invention of the present application. Exemplary prions include Scrapie (Sheep and goats), transmissible mink encephalopathy (TME), chronic wasting disease (CWD) in mule deer and elk, bovine spongiform encephalopathy (BSE) cattle, feline spongiform encephalopathy (FSE) in cats, exotic ungulate encephalopathy (EUE) in humans, Creutzfeldt-Jakob disease (CJD) in humans, Kuru in humans, Fatal familial insomnia (FFI) in humans and Gerstmann-Sträussler-Scheinker syndrome (GSS) in humans.

The present invention may be used to detect bioagents in a sample, such as viruses, prions, other microbes, biological mixtures of compositions and components, particles and their extracts, etc. as otherwise described herein. The present invention has utility in military applications, especially in field applications, in commercial applications, in agricultural applications and in research/medical applications (including the existence of air-born infections in the lungs of a patient). The present invention may be used to detect bioagents in the atmosphere (air), in water supplies, including standing water, in soil samples, etc.

By way of example, the present invention is useful for detecting numerous interactions between ligand and bioagent, including, for example, interactions between receptor and agonist/antagonist, between peptide and other peptides (peptide-peptide interaction), between antibody (monoclonal and polyclonal) and epitope on the bioagent (biomarkers, basic protein sequence, etc.), between polynucleotides (Watson-Crick base pairing or hybridization), as well as any other chemical or physical interaction (e.g., Van der Waals interactions) which may specify the binding or interaction of a bioagent with the ligand.

The term "tethered" is used to describe the attachment of the biological ligand onto the surface of the biosensor. The ligands are attached to the biosensor in a manner so that the portion of the ligand which binds to the bioagent is exposed on the surface. The ligands may be attached to the surface of the biosensor (preferably, a lithium tantalate chip) directly or indirectly by any means available. Ligands which are used in the present invention are complexed (coated or tethered through covalent, ionic, hydrophobic or other types of bonding) with the surface of the biosensor. This may include employing covalent bonding between ligand and sensor surface; e.g., the use of diazonium chemistry to attach the ligand to the sensor surface or through use of silicone chemistry. Some employ non-covalent bonding such as self-assembled monolayers; other approaches combine both covalent binding and non-covalent binding such as streptaviding-biotin interactions, wherein the streptavidin molecule is non-covalently attached to the sensor surface, and the biotin molecule is covalent bonding to the ligand and the streptavidin and biotin molecules are covalently bound to each other. Additionally, the attachment of ligands to sensor surface may be made through the process of physiosorption, which relies on Van der Waals forces to make non-covalent connections to the surface. Chemisorption, which uses covalent bonds, may also be used to attach or tether ligand to sensor surface. Simple adsorption may also be applicable to tether a ligand to the biosensor surface.

In certain applications, the surface of the piezoelectric material, a lithium tantalate wafer used in the present invention, is coated with a thin silicone dioxide surface or other surface which is created using standard methods such as sputtering techniques or more preferably, plasma enhanced chemical vapor deposition (PECVD) to produce a thin layer (about 500 Å to about 10,000 Å or more, in certain preferred aspects, about 5000 Å) as otherwise described herein. A ligand may be tethered to the silicone dioxide layer directly by covalent (chemisorption) or through non-covalent bonding (physisorption), or alternatively, the silicone dioxide layer may be further coated with a hydrophobic material (in certain embodiments, hexamethyldisilazine, or other hydrophobic material such as a liquid/semi-liquid hydrocarbon such as petrolatum or mineral oil, including other silicone materials) to provide a surface which is amenable to adsorption of a ligand as otherwise described herein. The hydrophobic layer on the silicone dioxide layer may be modified (covalently or non-covalently) using a chemical linker such as a functional silane compound, as otherwise described herein, which can covalently bond a ligand directly or bond a further linker (a complex linker) such as a binder protein (e.g., NeutrAvidin binding protein) which can bond certain molecules/moieties (biotin) which can be complexed with the ligand to tether the ligand indirectly to the surface of the SAW biosensor.

The term "adsorption" refers to a process that occurs when a gas or liquid solute accumulates on the surface of a solid or a liquid (adsorbent), forming a molecular or atomic film (the adsorbate). Adsorption is operative in most natural physical, biological, and chemical systems, including the present invention. Similar to surface tension, adsorption is a consequence of surface energy. In a bulk material, all the bonding requirements (be they ionic, covalent or metallic) of the constituent atoms of the material are filled. But atoms on a clean surface experience a bond deficiency, because they are not wholly surrounded by other atoms. Thus, it is energetically favourable for them to bond with whatever happens to be available. The exact nature of the bonding depends on the details of the species involved, but the adsorbed material is generally classified as exhibiting physisorption or chemisorption.

The term "physisorption" is used to describe a physical adsorption process in which there are van der Waals forces of interaction between a surface (solid) and a liquid or air layer. Physical adsorption is a type of adsorption in which the adsorbate adheres to the surface only through Van der Waals (weak intermolecular) interactions, which are also responsible for the non-ideal behaviour of real gases. Physisorption is characterised by the following:

Low ambient temperature, always under the critical temperature of the adsorbate;
Type of interaction: Intermolecular forces (van der Waals forces);
Low enthalpy: $\Delta H < 20$ kJ/mol;
Adsorption takes place in multilayers;
Low activation energy;
The energy state of the adsorbate is not altered;
The process is reversible.

In the present invention an exemplary physisorption approach to tethering ligands to the biosensor involves creates a silicon dioxide ($SiO_2$) layer on the biosensor wafer. This is the waveguide layer and varies in thickness (ranges from less than about 500 Å to about 20,000 Å or more, about 1000 Å to about 10,000 Å, about 1500 Å to about 7,500 Å, about 2500 Å to about 6500 Å, about 4000 Å to about 6000 Å, about 5000 Å), but is preferably about 5000 Å. Any method known in the art for depositing a silicon dioxide layer may be used, but a preferred approach utilizes plasma enhanced chemical vapor deposition (PECVD, Oerlikon Versaline, Switzerland) to provide the silicon dioxide layer. On top of the silicon dioxide layer a thin layer of a non-reactive liquid silicone material such as hexamethyldisilazane or other non-reactive, liquid alkyl silicone material such as an oligodialkylsiloxane, polydialkylsiloxane or other silicone, or a other non-reactive liquid may be used may be used.

The term "chemisorption" is used to describe a type of adsorption whereby a molecule adheres to a surface through the formation of a chemical bond, as opposed to the Van der Waals forces which cause physisorption. It is characterised by the following:

High temperatures;
Type of interaction: strong; covalent bond between adsorbate and surface;
High enthalpy: 50 kJ/mol $< \Delta H <$ 800 kJ/mol
Adsorption takes place only in a monolayer.
High activation energy
Increase in electron density in the adsorbent-adsorbate interface.
Reversible generally at high temperature.

The main way in which chemisorption is used in the present invention is that a linker molecule which may contain at least one hydroxyl (especially, Si—OH) binding group or other binding group (to bind to the surface of the biosensor) and at least one group which can bind an amine group, a carboxyl group, a hydroxyl group or a phosphate group are used to chemically link or tether a ligand to the surface of the biosensor. Other approaches include providing a linker comprising an amine, hydroxyl, carboyxl or phosphate binding group which itself is non-covalently physisorbed to the biosensor surface to, for example, a non-covalently bonded silicone such as hexamethyldisilazine which is itself non-covalently complexed to the $SiO2$ surface of the biosensor). Exemplary linkers for tethering a ligand to the biosensor include, for example, silanes containing reactive functional groups ("functional silane"), for example, 3-aminopropyltrimethoxysilane (amino group binding) and 3-glycydoxylpropyltriethoxysilane (carboxyl group binding), among others.

Several preferred approaches to tethering ligands may be taken in the present invention. These approaches may involve exclusively physisorption methods, chemisorption methods or combinations of physisorption and chemisorption methods. In a first physisorption method, a layer of silicon dioxide is produced on the surface of the biosensor using plasma enhanced chemical vapor deposition (PECVD) technology. Once the silicon dioxide layer is in place on the biosensor, a thin layer of hexamethyldisilazine (HMDS) or other inert silane is placed on the silicone dioxide layer. An antibody or peptide may be bonded (physisorbed) to the biosensor through the hexamethyldisilizane layer.

Alternatively, an antibody, peptide, fatty acid or carbohydrate may be bonded to a chemical linker (e.g. a functional silane) which is itself bonded (physisorbed) to a layer of hexamethyldisilazine (HMDS) and silicon dioxide to provide a tethered ligand on the biosensor of the present invention. This method combines both physisorption and chemisorption methods.

Still another approach for tethering a ligand to the biosensor of the present invention involves utilizing a linker protein, such as NeutrAvidin Binding Protein which itself binds to a biotinylated ligand, such as a peptide, amino acid or DNA molecule. In this aspect, the biosensor is first provided with a silicon dioxide layer to which is layered (physisorbed) a non-reactive silicone liquid, e.g., hexamethyldisilizane (HMDS). A thin layer of a functional silane, for example, 3-aminopropyltrimethoxysilane (amino group binding) and 3-glycydoxylpropyltriethoxysilane (carboxyl group binding), among others may be physisorbed to the hexamethylsilazine layer and the functional silane may be used to covalently link a binding protein (e.g. NeutrAvidin Binding Protein) to the biosensor. The NeutrAvidin Binding Protein may then be used to bind any biotinylated ligand. Additional approaches, or variations on the above approaches to tether virtually any ligand to the biosensor of the present invention are well within the ordinary skill of the routineer.

Figure 1B:
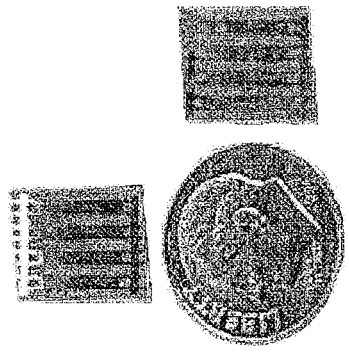
FIG. 1B is a photographic plan view of a pair of substrates or sensor wafers with IDT electrodes disposed thereon for making SAW measurements, showing the sensor wafers in scale compared to a dime coin (10 US cents); four aluminum delay lines are visible; one serves as the reference and three as the test delay lines.
Figure 1C:
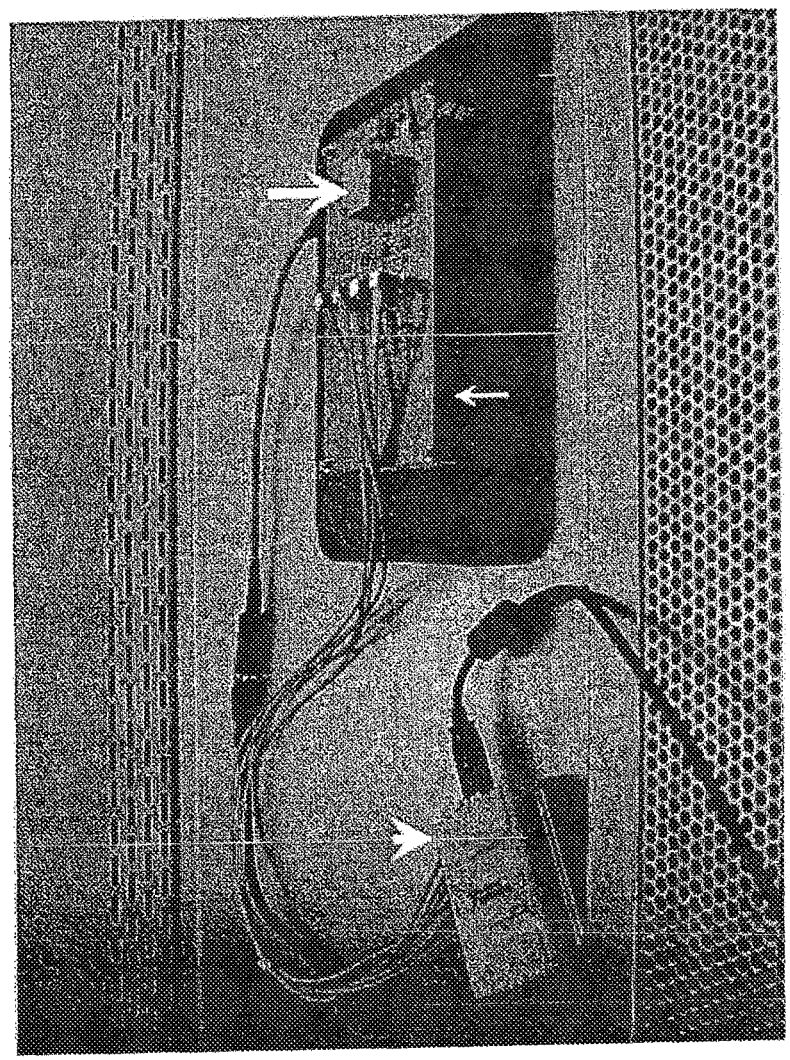
FIG. 1C is a photographic perspective view showing a SAW detection board (thin arrow) with the fluidic housing (thick arrow) and the output interface device (arrow head) to a laptop computer is shown.
Figure 1D:
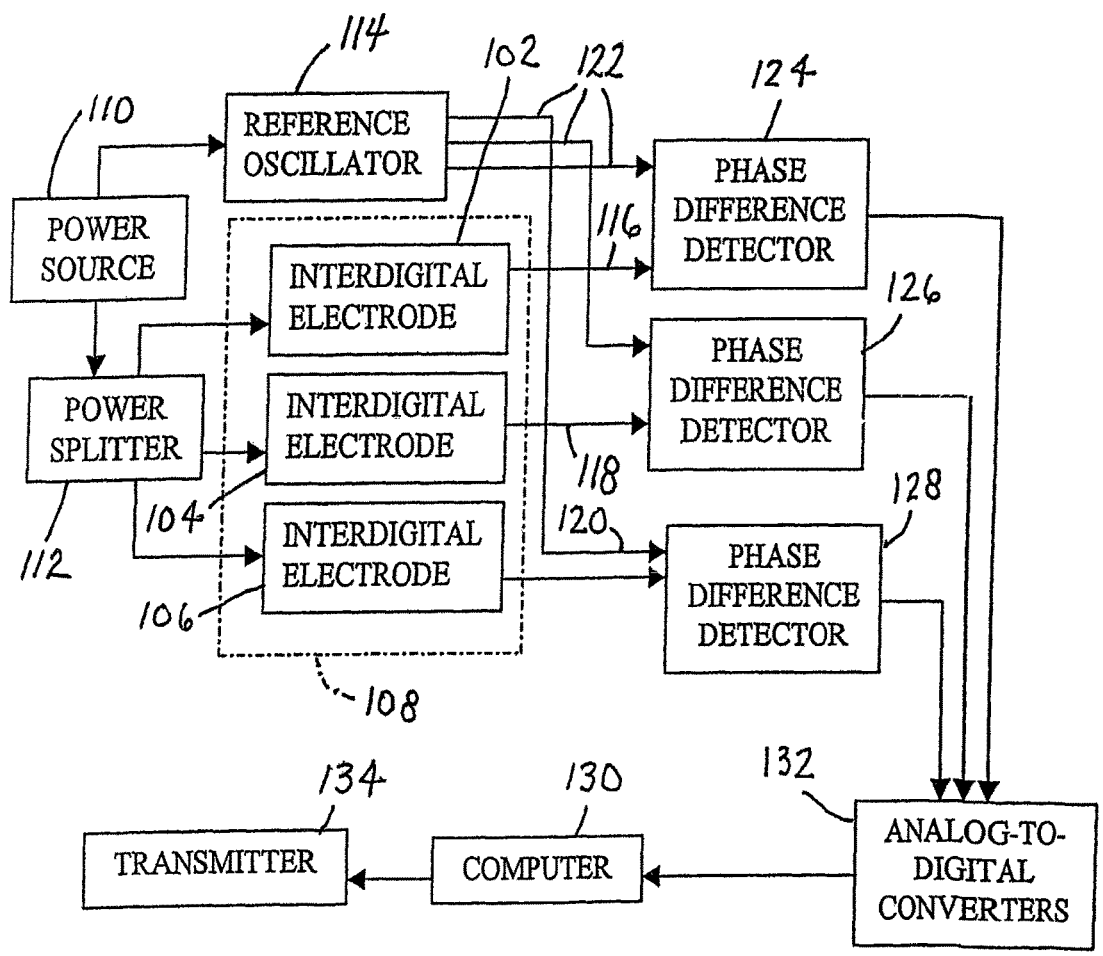
FIG. 1D is a block diagram of a SAW measurement assembly for making SAW measurements in accordance with the present invention.

The present invention is based on a biosensor apparatus featuring surface chemistries that are capable of transducing shear horizontal surface acoustic waves (SH-SAW) generated by piezoelectric materials such as lithium tantalate (LiTaO$_3$) when connected to an electrical circuit at defined frequencies. This technology is manufactured onto lithium tantalate wafers (or wafers from another piezoelectric material) that can be sectioned into functional units ("chips"). These units can be applied to a SAW detection board featuring a fluidic housing (described below) and a connection of the chip via aluminum delay lines to an output interface with a laptop computer for measurements of SAW. FIGS. 1B and 1C (attached) represent the functional unit. FIG. 1D is a block diagram of functional components of the ZAW measurement system.

As depicted in FIG. 1D, the components of the SH-SAW detector include three transducer elements 102, 104, 106 in the form of IDT electrodes disposed in a linear array on a substrate 108. Electrodes 102, 104, 106 are connected at inputs to a power source 110 via a power splitter 112. A reference oscillator 114 is provided, which may be used in part to generate the SH-SAW waves in the fluidic housing. As shown in FIG. 1B, reference oscillator 114 is disposed on the same substrate or chip as IDT electrodes 102, 104, 106. IDT electrodes 102, 104, 106 are each connected on an output side via a respective delay line 116, 118, 120 to a respective phase difference detector 124, 126, 128 exemplarily in the form of an IQ demodulator. Phase difference detectors 122, 124, 126 also receive input from oscillator 114 via a reference line 122. Phase difference detectors 122, 124, 126 are connected to a computer 130 via analog-to-digital converters 132. Computer 128 may be programmed, inter alia, to issue an alert signal via an output transmitter 134 upon detecting a disturbance in a standing wave indicating the presence of a target pathogen or toxic agent.

In FIG. 1B, the sensor wafer or substrate 108 is shown in scale compared to a dime coin (10 US cents); the four aluminum delay lines are visible; one line 122 serves as the reference and three others 116, 118, 120 (FIG. 1D) as the test delay lines. In FIG. 1C, the SAW detection board (thin arrow) with the fluidic housing (thick arrow) and the output interface device (arrow head) to a laptop computer is shown.

As described above, the surface of the sensor wafer can be complexed with ligands that are specific for any biological substance (for example, but not exclusively, a protein), free or as part of a larger complex (for example a virus, a spore, or a cell) for its detection when this substance, added in solution to the fluidic housing (the bioagent passes through small holes in the housing, which is permeable to the bioagent), is specifically recognized by its specific ligand on the surface of the sensor (see Claims below). Specific recognition (binding) results in a characteristic and quantifiable change of frequency that is captured using software applicable for such a purpose.

The present invention is directed to the detection of biological entities, such as viruses and cells, of both prokaryotic and eukaryotic nature, as well as prions and molecules using ligands specific for surface molecules of these entities. Such ligands can be for example antibodies or peptides. FIG. 1A shows one such example, in which a biotinylated antibody that is able to specifically recognize a virus is coupled to the LiTaO$_3$ surface of a SAW biosensor that has been coated with NeutrAvidin Biotin Binding Protein.

Preferred Embodiment

The following describes a preferred embodiment. The present invention is directed to the detection of viruses and other biological and chemical agents by SAW. In this embodiment, a Coxsackie virus, a member of the enterovirus family, which also includes polioviruses and hepatitis A virus (Palacios and Oberste, 2005) was the bioagent. Coxsackie virus infections are usually not of major health concern and possible fevers, headaches, and muscle aches typically self-dissolve after several days. Occasionally however, Coxsackie virus can cause serious infections, such as hand, foot and mouth disease, viral meningitis, encephalitis, myocarditis, and hepatitis, especially in newborns (Frydenberg and Starr, 2003; Tam, 2006). The primary objective is the Sin Nombre virus (SNV), a hantavirus member of the Bunyaviridae family of RNA viruses and a category A agent as defined by the National Institute of Allergy and Infectious Diseases (NIAID; website niaid.nih.gov) and other category A bioagents. SNV is transmitted by its reservoir host *Peromyscus maniculatus*, the deer mouse. Transmission happens by inhalation of aerosolized feces, urine, or saliva from the infected mice (Jay et al., 1997). The illness that ensues, hantavirus cardiopulmonary syndrome (HCPS), is characterized initially by mild flu-like symptoms, followed by rapid progression to respiratory distress, and can be fatal (Hjelle, 2002; Mertz et al., 2006). There is no established therapeutic regimen and treatment is only supportive. Preventive methods include attempts to minimize contact with the rodents since elimination of the virus is not realistic. Although human infections with hantaviruses are on the rare side, these agents have been classified by the Center of Disease Control (CDC) as potential agents for biologic terrorism due to their relative ease of production, the high susceptibility of large populations, and the limited treatment and vaccination strategies (Bronze et al., 2002).

In the present invention, the development and preliminary use of an SH-SAW biosensor able to detect category A viral agents operating at an input frequency of 325 MHz was a principal objective. Input frequencies may vary over a range of about 275 to 400 MHz, with 315-330 and 325 MHz being particularly useful. The present invention shows that the biosensor device of the present invention is sensitive and highly selective for its specific target. We also provide data in support of the biosensor's high reproducibility and its use in a real world scenario mimicking the exposure of an urban population to a viral agent, such as for example through the water system. The present invention indicates that this detection platform is highly versatile and robust and has significant medical or defense use.

2. MATERIALS AND METHODS 2.1. Fabrication of the 325 MHz SH-SAW Sensor

Wafer Preparation and Lithographic Deposition of IDT Layer:

The SH-SAW device was fabricated using metal evaporation and lift-off plasma enhanced chemical vapor deposition (PECVD), and reactive ion etching (RIE) techniques on a 36° y-cut, x-propagating lithium tantalate (LiTaO$_3$) crystal wafer of 510 µm thickness and 100 mm diameter. The wafer was cleaned in a barrel asher (PVA Tepla, Asslar, Germany) for 5 minutes, 600 Watts power and 900 mTorr of O$_2$, followed by dipping in 1 vol % hydrofluoric acid (HF) for 3 minutes, and rinsing in a cascade bath until the resistivity of the water was greater than 12 MOhm-cm followed by drying under N$_2$. The wafer layout was designed to include four IDT patterns with sets of transducers and delay lines. AZ2020 (AZ Electronic Materials, Branchburg, N.J., USA) negative-tone photoresist (PR) was applied using a spin coater with a Gyrset lid (Karl-Suss, Waterbury Center, Vt., USA) at 1300 and 3000 rpm/sec for 30 seconds each to achieve a thickness of 2.0 µm. The wafer was baked on a hotplate for 60 seconds at 110° C. and cooled to room temperature on a metal surface. Because of the pyroelectric nature of $LiTaO_3$ it was necessary to remove residual electric charge by dipping the wafer in de-ionized water and drying under $N_2$. The PR was exposed to i-line UV light at 365 nm for 6 seconds at 14 mW/cm². The wafer was re-baked on a hotplate at 110° C. for 60 seconds followed by a 1 minute developing time in a 300 MIF developer (AZ Electronic Materials) and rinsing in de-ionized water. The wafer was metallized with 5000 Å aluminum using an electron-beam evaporator (Temescal, Wilmington, Mass., USA). The deposition rate was 3 Å/sec for 500 Å and then 5 Å/sec for 4500 Å. The wafer was placed in an acetone bath to lift off the PR and excess aluminum. An acetone spray was used to remove the PR between the IDT fingers, followed by rinses in methanol, isopropyl alcohol, and de-ionized water. This procedure was repeated for the metallization of the ground plane, buss lines, and contact pads.

Deposition of the Waveguide Layer and Final Preparation:

A 5000 Å silicon dioxide ($SiO_2$) film was deposited onto the entire wafer using PECVD (Oerlikon Versaline, Pfaeffikon, Switzerland) at 150° C. for 410 seconds. The oxide was coated with hexamethyldisilazane (HMDS) in a vacuum oven at 100° C. for 30 minutes. AZ4330 positive-tone PR (AZ Electronic Materials) was spin coated onto the wafer at 2000 rpm and 3000 rpm/sec for 30 seconds each. The wafer was baked on a hotplate at 90° C. for 90 seconds, exposed for 48 seconds at 20 mW/cm² (at 400 nm), and developed in a 300 MIF developer for 3 minutes. A photoresist mask was used to "open" the $SiO_2$ and expose the electrical contact pads. The $SiO_2$ was etched by RIE (Oerlikon Versaline) for 1500 seconds (p=40 mT. CHF3=45 sccm, O2=5 sccm, P=125 watts, DC bias=712 volts). The wafer was diced using a resinoid dicing blade. The PR was removed from the individual die by rinsing in acetone, methanol, and isopropanol.

2.2. Virus Production and Preparation

Viral work was conducted in Biosafety Level 2 (Coxsackie virus B4) or Level 3 (SNV) facilities at the University of New Mexico School of Medicine. The JVB strain of Coxsackie virus B4 was purchased from ATCC (Manassas, Va., USA). Buffalo Green Monkey Kidney (BGMK) cells were purchased from Diagnostic Hybrids, Inc. (Athens, Ohio, USA). BGMK cells were grown to confluency in DMEM, 2 mM L-glutamine, 10 mM HEPES, 26.8 mM sodium bicarbonate, and 10% fetal bovine serum. After removal of culture media, BGMK cells were inoculated with Coxsackie virus B4 for 1 hour at room temperature and grown in a serum free media, Opti PRO SFM (GIBCO, Grand Island, N.Y., USA) supplemented with 4 mM L-glutamine. Upon reaching 100% cytopathic effect (CPE), the media was centrifuged in a sealed rotor for 5 minutes at 3000 rpm and the supernatant was stored at −20° C. The viral titer was determined by serial dilution and growth in BGMK cells. The virus was inactivated with 2.0 Mrads of gamma radiation using a Gammacell 40 (Atomic Energy of Canada, Ltd., Kanata, Ontario, Canada) and concentrated by lyophilization and resuspension in distilled water.

SNV particles were purified from the supernatant of VeroE6 monkey kidney cells (ATCC) infected with SNV at a multiplicity of infection of 0.1 for 1 hour. After 9 days the media was subjected to ultracentrifugation using Optiprep density gradients in phosphate buffered saline (PBS) (Axis-Shield, Norton, Mass.) and the isolated virus was inactivated by UV. The amount of SNV particles was quantified by determining the SNV nucleocapsid (SNV-N) protein concentration (not shown). SNV particle number was calculated based on the following parameters pertaining to the SNV-N protein: SNV-N has a mass of 50 kD; thus 1 mol (6.02×$10^{23}$)=50,000 grams; thus one SNV-N protein=$8.3 \times 10^{-11}$ nanograms. There are ~$10^5$ SNV-N proteins per SNV particle; thus $8.3 \times 10^{-6}$ nanograms of SNV-N=one SNV particle. Using these calculations, 1 nanogram of SNV-N protein corresponds to ~120,000 SNV particles. Purified Herpes Simplex virus type 1 (HSV-1) was a kind gift of Dr. Stephen Young at TriCore Laboratories (Albuquerque, N. Mex., USA).

2.3. Preparation of Antibodies and Adsorption to the SAW Biosensor

The IgG2a isotype monoclonal antibody (mAb) directed against the JVB strain of Coxsackie virus B4 was produced by the 204-4 hybridoma cell line (ATCC). The mAb was labeled with biotin using the EZ-Link NHS-PEO Solid Phase Biotinylation Kit and Spin Column featuring the SwellGel Disk technology (Pierce, Rockford Ill., USA). The mAb was added to the gel at 2 mg/ml for 10 minutes followed by incubation in NHS-PEO4-Biotin for 30 minutes at room temperature and column spinning. The biotin labeled antibody was eluted from the column with 0.2 M Imidazole in PBS. Single chain Fv antibodies (scFv) directed against SNV have been previously selected from a phage antibody library, and are specific for the SNV-G1 glycoprotein exerting no cross-reactivity with glycoproteins from other hantaviruses (Velappan et al., 2007). These scFv antibodies were left unmodified and directly adsorbed to the biosensor.

The SAW devices were cleaned in acetone, methanol, and isopropanol, then treated by ultrasonication in 95% ethanol, rinsed in distilled water, followed by exposure to UV-ozone for 10 minutes in a UVOCS UV-Ozone cleaner (UVOCS Inc., Montgomeryville, Pa., USA). For the antibody directed against the Coxsackie virus B4, the oxide layer of the test delay lines of the SAW device were coated in a non-covalent physisorption process with 0.25 mg/ml of NeutrAvidin Biotin Binding Protein (Pierce) in PBS for 30 minutes at room temperature. The device was washed 3 times with PBS and 1 time with distilled water, and dried using nitrogen. The biotin labeled 204-4 mAb was adsorbed to the NeutrAvidin Biotin Binding Protein at 0.25 mg/ml in PBS for 30 minutes at room temperature. For the detection of SNV, anti-SNV-G1 scFv at 0.25 mg/ml was directly adsorbed to the SAW device for 30 minutes at room temperature. After coating with the antibodies, the biosensor devices were washed 3 times with PBS and 1 time with distilled water, followed by nitrogen drying.

2.4. SAW Detection of Coxsackie and SNV

For display and acquisition of the digitized voltage data from the sensor platform, a custom LabVIEW (National Instruments; website ni.com) program was developed. The data from each of the delay lines were acquired simultaneously and the voltage information was converted back to the phase. Data from the reference line were subtracted from the data from the test lines for each time point measured and continuously saved to disk in spreadsheet format. The data for the quantitative measurements of viral detection presented in this study refer to the phase differential mass shift (Δφ) and are displayed on a graph as a function of time of acquisition. Multiple data points per time are recorded during this process. The SAW device was assembled in a static cell with a 325 MHz input frequency from a power supply. The chamber (fluidic housing) was covered with 0.4 ml of PBS or medium and the phase differential was stabilized for at least 100 seconds. 0.1 ml of solution was removed and replaced with 0.1 ml of virus containing solution. Virus was typically detected within ~15 seconds as observed by an elevation of the signal Δφ (in degrees on the y-axis) along the time plot x-axis). The detection run was allowed to reach stabilization of the phase differential, typically after ~2 minutes. The virus containing solution can be removed and the run can be continued with 0.4 ml of PBS until stabilization. Δφ can either be measured at stabilization after agent injection or after removal of the agent and re-stabilization in buffer. A detailed description of the former process is given in the legend for FIG. 2.

2.5. Statistics

All phase differential mass shift (Δφ) data points were generated in at least duplicate and sometimes up to five tests. Data is presented as average±standard errors (SE). The statistical difference between groups of average measurements of phase differential mass shifts Δφ were determined using the students t-test. $P<0.05$ was considered to be statistically significant.

3. RESULTS 3.1. Initial Testing of the SAW Detector

The major objective of this study was to couple the characteristics of SAW with the selectivity of antibodies to detect viruses of high medical and bio-warfare importance. FIG. 1A depicts the overall schematic concept of our device. FIG. 1B shows the miniature size of the wafer sensors, i.e. approximately 15 by 20 mm, featuring 4 delay lines, of which one is used as the reference line, while the others are used as test lines. FIG. 1C shows the SAW detection board with the fluidic housing (containing the wafer) and the output interface device to a laptop computer. The sealed fluidic housing connected the IDTs to the electrical input/output system of the static cell; a power supply provided an input frequency of 325 MHz. The phase differential mass shift Δφ (expressed in degrees) was captured on the laptop computer using a custom LabVIEW program.

Figure 2:
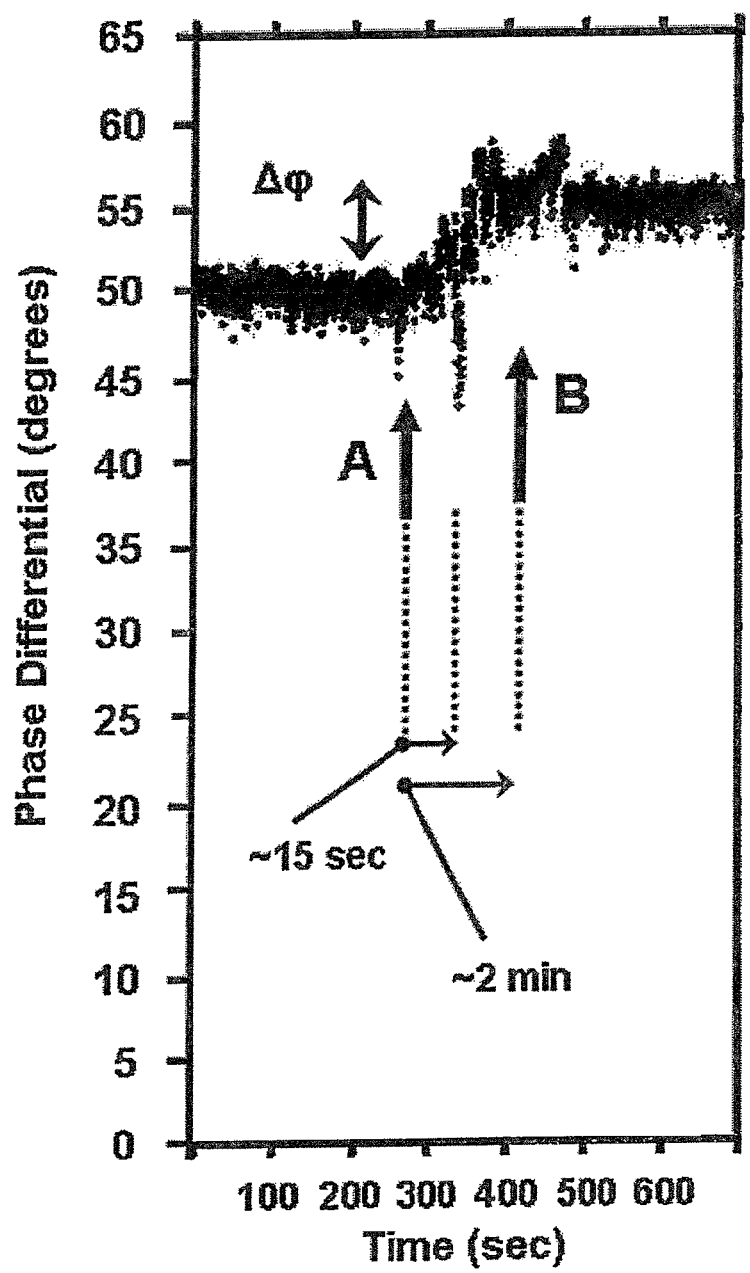
FIG. 2 is a graph showing a detected phase differential as a function of time during operation of a SAW sensor assembly in accordance with the present invention. More particularly.

Viral detection was performed by immobilizing antibodies onto the sensor. The test delay lines were either directly coated with unlabeled antibodies (for SNV) or with NeutrAvidin Biotin Binding Protein followed by botinylated antibodies (for Coxsackie virus B4). FIG. 2 represents a typical phase differential plot generated by exposing the sensor to $1.8 \times 10^4$ SNV particles per μl. The plot shows the PBS buffer calibrated surface at ~50 degrees, injection of the virus containing solution at ~280 seconds (measured on the x-axis), and maximal signal at ~420 seconds (~2 minutes after agent injection). Detection was evident at ~15 seconds after addition of the agent and resulted in an overall Δφ of ~5 degrees (measured on the y-axis). Thus, Δφ can be measured shortly after agent injection and the overall process can be performed within minutes. All subsequent data for the quantitative measurements of viral detection refer to the change in Δφ as described in FIG. 2.

3.2. Quantitative and Selective Detection of Coxsackie B4 and Sin Nombre Virus (SNV)

Figure 3:
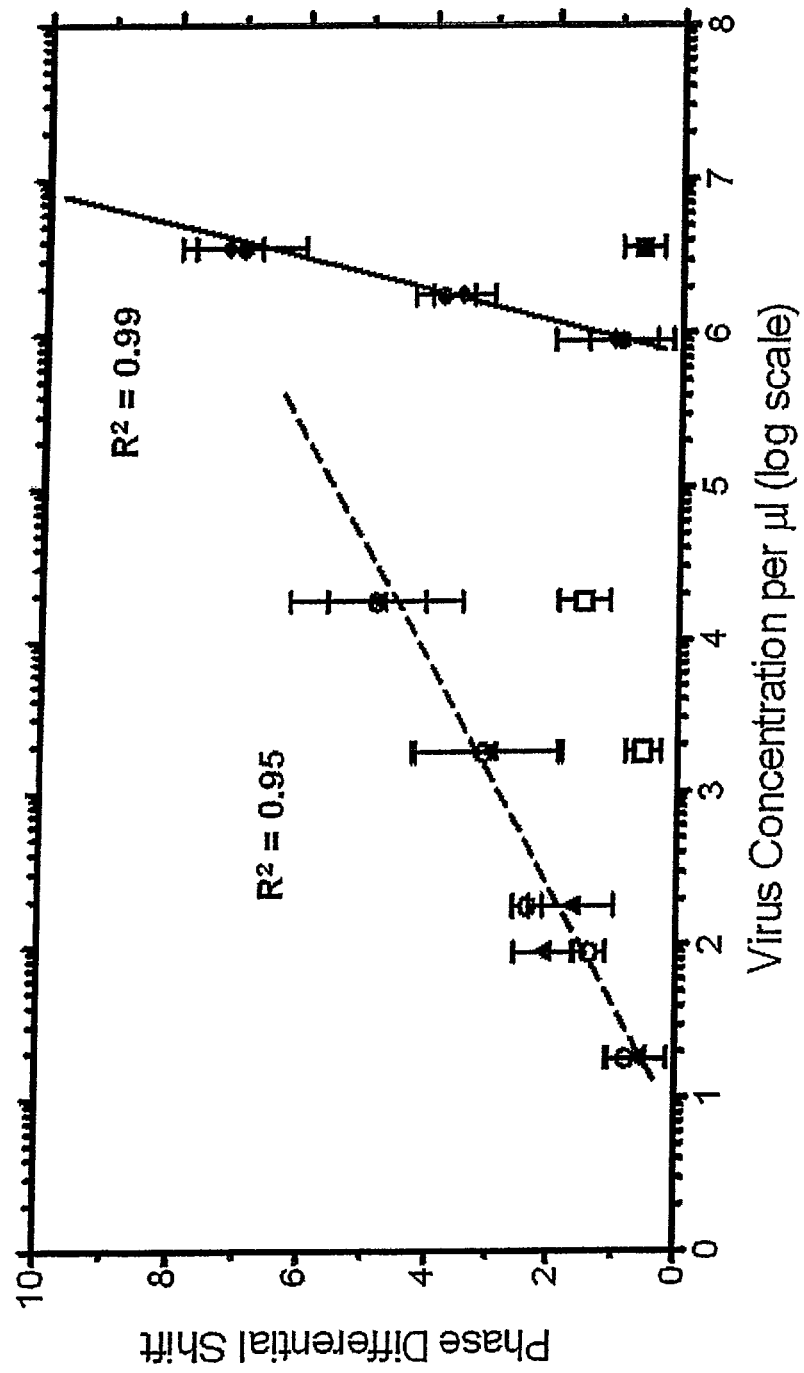
FIG. 3 is a graph of phase differential shift as a function of virus concentration, depicting the detection of Coxsackie virus B4 and SNV using the SAW biosensor, in accordance with the present invention. Data was acquired as described in FIG. 2 and in the text. The plots show the shifts in phase differential (degrees) on the y-axis as a function of increasing viral particle concentrations (in virus/µl) on the x-axis. Each data point represents an average of 2-5 measurements±standard errors. ●=Coxsackie virus B4; ♦=Coxsackie virus B4+HSV-1; ■=HSV-1 alone for the Coxsackie virus experiments; ▲ SNV; ○=SNV+HSV-1; □=HSV-1 alone for the SNV experiments. The solid and dotted lines represent the best fit models and coefficient correlations ($R^2$) for Coxsackie virus B4 (●) and SNV (▲), respectively.

The SAW biosensor was used in a series of experiments for the detection of Coxsackie virus B4 particles (FIG. 3). Increasing concentrations of viral particles ranging from $9 \times 10^5$ to $3.6 \times 10^6$ viruses per μl were analyzed as described in FIG. 2. A was recorded for each concentration and resulted in a dose-dependent increase with A values ranging from 0.95±0.54 to 6.99±0.96 (FIG. 3; data set to the right). There was a linear relationship between viral load and Δφ for this range of viral particles with a correlation coefficient $R^2$ of 0.99. To determine the selectivity of the biosensor for its target in the presence of a confounding agent, the experiments were repeated using admixtures of Coxsackie B4 and HSV-1 viruses. HSV-1 was spiked into the Coxsackie virus preparations at equal final concentrations as for Coxsackie B4 and the previous experiments were repeated. HSV-1 did not affect the selectivity for Coxsackie B4, yielding similar Δφ values ranging from 1.09±0.66 to 7.24±0.36. The relationship between viral load and Δφ remained linear with a correlation coefficient $R^2$ of 0.98. In these spiking experiments, where HSV-1 was used as a confounding agent, the Δφ for HSV-1 at a concentration of $3.6 \times 10^6$/μl was 0.64±0.33, indicating that the biosensor did not detect HSV-1.

Next, we used the SAW biosensor to detect an agent of high medical concern, i.e. SNV, a member of the hantavirus genus of the family Bunyaviridae and an NIH-designated bioagent of category A (Bronze et al., 2002). Concentrations of $1.8 \times 10^1$ to $1.8 \times 10^4$ viral particles per μl resulted in Δφ of 0.63±0.49 to 4.85±0.77 (FIG. 3; data set to the left). The measured values displayed variation with some overlap as shown by their standard deviations. This can be attributed mainly to factors related to microfabrication reproducibility for the current sensor system. Our studies indicate that sensitivity is a function of the absolute thickness of the silicon dioxide waveguide. We have determined that thickness variations of 5% lead to a ~8% alterations in detection sensitivities (data not shown). However, our calculated waveguide variations for the current sensors are approximately 1-2%, which is unlikely to contribute to the observed experimental variation. In addition, variations in the lithographic process which guides the geometry of the IDTs on our sensors can influence their sensitivity. We are currently gathering data to quantify this potential problem and may change the process from contact to projection lithography. Nevertheless, the data means resulted in a linear relationship between viral load and Δφ for this range of viral particles with a correlation coefficient $R^2$ of 0.95. Similar to the experiments with Coxsackie virus, the selectivity of the SAW biosensor for SNV was not diminished by the presence of confounding HSV-1 at equal concentrations. The corresponding Δφ ranged from 0.78±0.30 to 4.83±1.36 and the relationship between viral load and Δφ remained linear with a correlation coefficient $R^2$ of 0.97. For this set of experiments, the biosensor was marginally sensitive to HSV-1 alone, resulting in Δφ values of 0.56±0.27 and of 1.51±0.40 for viral concentrations of $1.8 \times 10^3$/μl and $1.8 \times 10^4$/μl, respectively.

Based on the lowest concentrations tested for both viral agents, which in both cases yielded Δφ above values obtained with HSV-1, the sensitivity for the antibody directed against SNV was approximately $50 \times 10^4$-fold greater compared to the sensitivity of the antibody directed against Coxsackie B4 virus. The slopes for the detection of Coxsackie virus and SNV were markedly different (FIG. 3). This could be due to multiple factors including the deposition efficiency and corresponding site density of the capturing agents coated on the biosensor surface, in this case the anti-Coxsackie B4 and anti-SNV antibodies, which determines the number of binding sites available to specific viral ligands, in this case the Coxsackie B4 JVB epitope and the SNV-G1 glycoprotein. Similarly, differences in sensitivity can be explained by its dependence on the affinity between an antibody and its corresponding antigen. This leaves room for the development of better immunological tools with higher sensitivities. Accordingly, we are currently employing phage display to identify high affinity protein-peptide interactions to increase the sensitivity for viral particles.

3.3. Virus Detection in Complex Solutions

Figure 4:
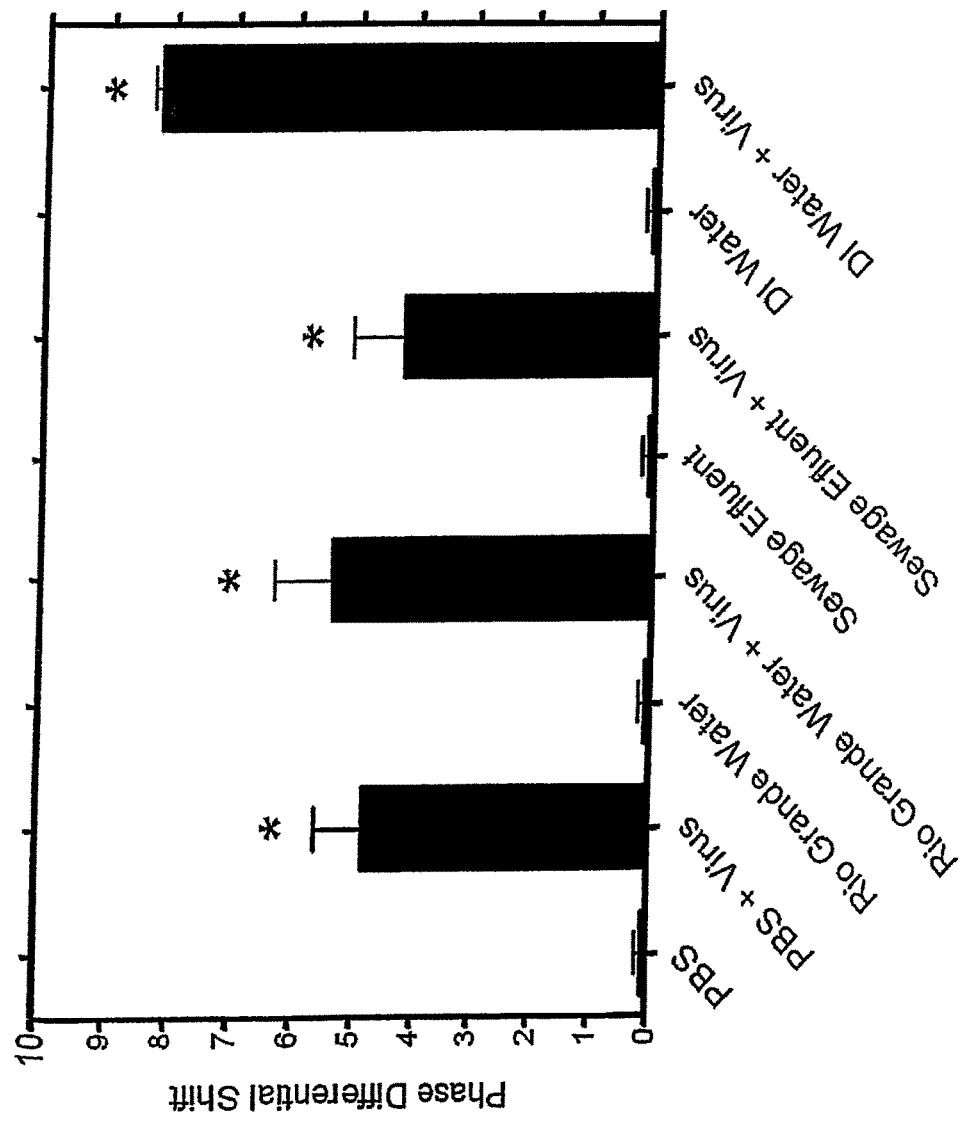
FIG. 4 is a bar graph phase differential shift as a function of test solutions, showing detection of SNV in complex solutions using the SAW biosensor. SNV viral particles were spiked into distilled (DI) water, phosphate buffered saline (PBS), sewage effluent, or Rio Grande water for a final concentration of $1.8 \times 10^4$ viral particles/µl. Data was acquired as described in FIG. 2 and in the text. The plots show the shifts in phase differential (degrees) on the y-axis as a function of solution input on the x-axis. Each data point represents an average of 2 measurements with ±standard errors. Stars denote statistical significance ($p<0.05$) over background (no virus) solutions using student's t-test.

The SAW biosensor was applied to a real world scenario which could mimic the exposure of an urban population to a viral agent, such as for example through the water system. In these proof-of-principle experiments, SNV particles were spiked into 0.4 ml of either the sewage effluent water of the City of Albuquerque N. Mex., water taken from the Rio Grande River in Albuquerque, or distilled water or PBS as controls at a final concentration of $1.8\times10^4$ virus/μl. As shown in FIG. 4, all of the control solutions lacking viral particles showed similar background levels of Δφ in the order of 0.1. The SAW biosensor showed the highest sensitivity when the viral particles were spiked into distilled water, displaying a Δφ of 8.21±0.11 degrees (~82× over background). The Δφ for virus spiked into PBS, Rio Grande River water, and sewage effluent water were similar, i.e. 4.85±0.77, 5.36±0.93, and 4.22±0.84, respectively, corresponding to ~48×, 54×, and 42× fold differences over background, respectively. The Δφ values of all virus spiked solutions were significantly ($p<0.05$) higher than their background solutions without virus, as determined by simple students t-test. In addition, these experiments in complex solutions collectively indicate a high re-usability of the sensor resulting in reproducible data. The data in FIG. 4 represent duplicate experiments using regenerated sensors after treatment with organic solvents, ultrasound, and UV-ozone. Nevertheless, multiple antibody re-coating and re-testing procedures led to Δφ measurements for the specific target within standard errors of ~13% of the mean.

4. DISCUSSION

Antibody based detection by SAW has previously been reported for cellular microorganisms, such as bacteria. We recently reported on a 103 MHz operated SAW sensor to detect bacterial spores of *Bacillus thuringiensis*, a pathogen simulant for *Bacillus anthracis*, at or below inhalational infectious levels (Branch and Brozik, 2004). In that study we developed suitable chemistries to orient the antibodies on the sensor using protein G on two different waveguide materials, i.e. polyimide and polystyrene. We found that polyimide had a lower mass detection limit leading to highly selective bacterial detection as shown by the absence of binding to the control agent *Bacillus subtilis*. Similarly, Berkenpas and colleagues recently described a SAW biosensor that was coated with a polyclonal antibody specific for the toxigenic *Escherichia coli* O157:H7 bacterium which causes hemorrhagic colitis and hemolytic uremic syndrome (Berkenpas et al., 2006). These authors reported Δφ responses of approximately 14 degrees representing a 7-fold difference over background control antibodies against trinitrophenyl (TNP) hapten.

In contrast, detection of viral and other agents by antibody coupled SAW is largely absent from the literature. In one of the few published studies Tamarin and colleagues developed a SAW sensor similar to the one presented here, and used it to study physical parameters of specific binding between antibodies and M13 bacteriophages (Tamarin et al., 2003). In addition, Tassew and Thompson reported on the detection of the human immunodeficiency virus (HIV) type 1 Tat protein using immobilized trans-activation-responsive RNA elements and various Tat peptide fragments (Tassew and Thompson, 2003). Thus, our study represents a contribution to the field of specific detection of viral agents by the SAW technology based on protein interactions (antibodies).

Collectively, our experiments using Coxsackie B4 and SNV indicate a high sensitivity and selectivity of the SAW detector for its targets. Importantly, selectivity was not compromised by the presence of confounding and related factors, such as other viruses, indicating the potential use of this device for the specific detection in complex solutions. In a previous study we have used quantitative (real time) reverse transcriptase polymerase chain reaction (RT-PCR) specific for the S segment of SNV RNA to determine viral copy number in bodily fluids, such as blood plasma and tracheal aspirates (Xiao et al., 2006). Assay sensitivity was ~5000 RNA copies (corresponding to viral particles) per ml, but the material to be tested had to be processed. Pre-processing of analyte is also necessary for other established techniques, including enzyme linked immunosorbent assay (ELISA) and surface plasmon resonance (SPR). Furthermore, SPR technology is still relatively costly and not amenable to a portable format. In contrast, our SAW platform allows detection of viral bioagents without pre-processing of the analyte, and can be developed into a portable field application. The SAW biosensor was able to detect at least 7000 SNV particles. Although the minimal infectious dose of SNV necessary to establish a successful human infection remains unknown, this number is substantially lower than the dosage found in hantavirus infected humans suffering from HCPS (Xiao et al., 2006).

An important and novel finding of this study is the detector's application to a real world scenario using water obtained from the sewage system and from a river of an urban area. This is a real world possibility for planned or accidental bioagent distribution and can lead to mass exposure within the population, which in turn can lead to an extensive health crisis (Bronze et al., 2002; www.cdc.gov). Naturally occurring water bodies, such as rivers are admittedly very complex solutions containing perhaps millions of different organic and inorganic molecules. It is thus noteworthy that our antibody-coated biosensor was able with high selectivity to detect the correct agent against this complex background. While the likelihood of detection in a large body of water could be increased by concentration strategies, such a procedure would compromise two important strengths and advantages of the current system, i.e. the hand-held, portable nature, and the absence of analyte pre-processing. In addition, it remains to be shown whether a flow-through set-up that continuously monitors dilute samples vs. the static set-up reported here would increase the representative power of the analyzed sample. In a static setting changes in phase differential due to the added agent and buffer are accumulating, while in a flow-through setting the sensor would return back to the original phase differential of the carrier buffer, as the sample passes through the sensor. Comparisons between these approaches are currently under investigation in our laboratory.

Together, these data, and the results which are presented in Table 1, below, indicate that the sensor of the present invention may be used under field conditions and warrant further efforts into the development of inexpensive portable devices for field operation. This includes a hand-held battery operated and self-contained version of the present invention.

5. FURTHER EXAMPLES

The following ligands (presented in Table 1) have been successfully adsorbed to the SAW biosensor and the corresponding analysis using the biosensor/SAW technology as described above have been successfully implemented. The analytes (Table 1) were detected selectively, partially in the presence of confounding agents (agents which are provided to make it more difficult to evidence binding and analysis by the present invention).

Importantly, the analytes were rapidly detected in real-time and in complete absence of any pre-processing steps.

Methods of Tethering Ligand to SAW Biosensor

The surface of the SAW biosensor can be prepared for ligand binding using the following different procedures/methods which are applicable to different ligands as listed in the Table. The sequential steps are generally described for each Method (also, see above), and the letters are listed in the third column (under "Absorption Mode") for the corresponding ligands. The following coats are deposited onto the lithium tantalate (LiTaO$_3$) surface.

Method A

1. A layer of silicone dioxide is etched/deposited onto the surface of the lithium tantalate surface. This is the waveguide layer and is ~5000 Å thick.
2. A thin layer of hexamethyldisilazane (HMDS) is deposited onto the surface of the silicon dioxide.
3. Ligand is deposited onto the HMDS layer non-covalently.

Method B

1. A layer of silicone dioxide is etched/deposited onto the surface of the lithium tantalate surface. This is the waveguide layer and is ~5000 Å thick.
2. A thin layer of hexamethyldisilazane (HMDS) is deposited onto the surface of the silicon dioxide.
3. A thin layer of 3-aminopropyltrimethoxy silane (amino group binding) or 3-cycydoxylpropyltriethoxy silane (carboxyl group binding) as a functional silane is deposited onto the HDMS layer.
4. Ligand is bound to the functional group (amine or carboxyl group) of the silane covalently.

Method C

1. A layer of silicone dioxide is etched/deposited onto the surface of the lithium tantalate surface. This is the waveguide layer and is ~5000 Å thick.
2. A thin layer of hexamethyldisilazane (HMDS) is deposited onto the surface of the silicon dioxide.
3. A thin layer of 3-aminopropyltrimethoxy silane (amino group binding) or 3-cycydoxylpropyltriethoxy silane (carboxyl group binding) as a functional silane is deposited onto the HDMS layer.
4. A thin layer of NeutrAvidin Binding Protein (0.25 mg/ml—range of 0.05 mg/ml to 1 mg/ml, about 0.1 mg/ml to about 0.75 mg/ml, about) in phosphate buffered saline is layered onto the layer of functional silane. A covalent linkage between the protein and functional silane results.
5. Ligand is bound to the functional group (amine or carboxyl group) of the silane covalently.

TABLE 1

| Ligand | Analyte (recognized by ligand) | Adsorption Mode |
|---|---|---|
| Antibodies | | |
| Anti-Coxsackie virus monoclonal antibody (mouse IgG2a) | Coxsackie virus B4 (JVB strain) | Methods A, B, Method C (if ligand biotinylated) |
| Anti-Sin Nombre virus (SNV) G1 glycoprotein (single chain Fv, scFv from phage display) | Sin Nombre virus (SNV) | Methods A, B, Method C (if ligand biotinylated) |
| Anti-Herpes Simplex virus 1 (HSV-1) antibody (polyclonal) | Herpes Simplex virus 1 (HSV-1) | Methods A, B, Method C (if ligand biotinylated) |
| Anti-αvβ3 integrin antibody | αvβ3 integrin | Methods A, B, Method C (if ligand biotinylated) |
| Anti-Interleukin-12 (IL-12) monoclonal antibody (mouse IgG1) | Human Interleukin-12 (IL-12) | Methods A, B, Method C (if ligand biotinylated) |
| Anti-Interleukin-6 (IL-6) polyclonal antibody (goat IgG) | Human Interleukin-6 (IL-6) | Methods A, B, Method C (if ligand biotinylated) |
| Peptides | | |
| 18 different peptides (cyclic, 9 amino acids; from phage display) 18 different peptides (cyclic, 9 amino acids; from phage display) | Sin Nombre virus (SNV) | Methods A, B, Method C (if ligand biotinylated) |
| 1) JC-1 = CLVRNLAWC SEQ ID No 1 | | |
| 2) JC-2 = CSASTESLC SEQ ID No 2 | | |
| 3) JC-3 = CQTTNWNTC SEQ ID No 3 | | |

TABLE 1-continued

| Ligand | Analyte (recognized by ligand) | Adsorption Mode |
|---|---|---|
| 4) JC-4 = CKSFTTTRC SEQ ID No 4 | | |
| 5) JC-5 = CAEPNSHRC SEQ ID No 5 | | |
| 6) G1-0 = CKQTTNRNC SEQ ID No 6 | | |
| 7) G1-1 = CQATTARNC SEQ ID No 7 | | |
| 8) CSAGAPEFC SEQ ID No 8 | | |
| 9) CTQSGLLSC SEQ ID No 9 | | |
| 10) CKSFTTTRC SEQ ID No 10 | | |
| 11) CTYPYPKFC SEQ ID No 11 | | |
| 12) CKSTFSPNC SEQ ID No 12 | | |
| 13) CTSAAVHMC SEQ ID 13 | | |
| 14) CQPHLPWHC SEQ ID 14 | | |
| 15) CQWPGQSGC SEQ ID No 15 | | |
| 16) CNSSSPTAC SEQ ID No 16 | | |
| 17) CHQLMQNLC SEQ ID No 17 | | |
| 18) CIQSGLLS SEQ ID No 18 | | |
| 10 different peptides (cyclic, 9 amino acids; from phage display) | Andes virus | Methods A, B, Method C (if ligand biotinylated) |
| 1) C5-1 CPKLHPGGC SEQ ID No 19 | | |
| 2) C5-2 CPMSQNPTC SEQ ID No 20 | | |
| 3) C5-3 CTVGPTRSC SEQ ID No 21 | | |
| 4) B9-1 CPSNVNNIC SEQ ID No 22 | | |
| 5) B9-2 CMQSAAAHC SEQ ID No 23 | | |
| 6) B9-3 CNSHSPVHC SEQ ID No 24 | | |
| 7) B9-4 CKSLGSSQC SEQ ID No 25 | | |
| 8) B9-5 CPAASHPRC SEQ ID No 26 | | |
| 9) B9-6 CEKLHTASC SEQ ID No 27 | | |
| 10) B9-7 CSLHSHKGC SEQ ID No 28 | | |
| 1 peptide (linear, 16 amino acids; from phage display) DTRACDVIALLCHLNT SEQ ID No 29 | Dengue virus | Methods A, B, Method C (if ligand biotinylated) |
| Nucleic Acids | | |
| (a) SNV-N (nucleocapsin protein) Capture DNA | Sin Nombre virus (SNV) RNA | Method C |
| 1) CCCTAGAGATGCTGCATTGGCAACTAA SEQ ID No 30 | | |
| 2) TTACAGGTTGATGAGTCAAAAGTTAGT SQ ID NO 31 | | |
| 3) TTACAGGTTGATGAGTCAAAAGTTAGTGATAT TGAGGACC SEQ ID NO 32 | | |
| (b) SNV-M (glycoprotein) Capture DNA | | |
| 1) CCTGATCAAAATGGACAAGGTTTAATGAGAATAGCTGGGC SEQ ID No 33 | | |

TABLE 1-continued

| Ligand | Analyte (recognized by ligand) | Adsorption Mode |
|---|---|---|
| 2) TTTCATGCTCACATTATTCTACAGAAT SEQ ID No 34 | | |
| 3) TTTCATGCTCACATTATTCTACAGAATCAAAATTCAAGT SEQ ID No 35 | | |
| Biotinylated BRCA1 capture DNA (single-stranded; 30 bases) 5'-CCTGGATAATGGGTTTATGAAAAACACTTT SEQ ID No 36 | BRCA1 DNA (single-stranded; 60 bases) | Method C |

Physisorption = Direct adsorption on silicon dioxide
Silane = 3-aminopropyltrimethoxy silane
NAB = NeutrAvidin Binding Protein

6. CONCLUSIONS

Detection of biological agents and their products in the context of bio-warfare, human health and agricultural production are important tasks with a current sense of urgency. Applications include the detection of agents and their products in the environment after planned or accidental distribution into the soil or water bodies, such as swimming pools, rivers, aquifers, and the sewage system, especially in highly urbanized areas. Another application is the detection of agents and markers thereof in human fluids and tissues for the correct diagnosis and treatment stratification of patients. Towards this end, we have developed a SAW biosensor that is capable of rapidly detecting viral agents with high selectivity and sensitivity for at least two different targets, i.e. Coxsackie B4 virus and the category A bioagent SNV. Our detector combines the sensitivity of surface acoustics with the selectivity of antibody-antigen recognition and offers a highly versatile platform for the detection of other viral agents and their products. Further, the results obtained in this study emphasize the possibility for future, more refined developments and applications of portable SAW based technology in the fields of viral medicine and environmental surveillance.

REFERENCES

Berkenpas, E., Millard, P., Pereira da Cunha, M., 2006. Biosens. Bioelectron. 21, 2255-62.
Branch, D. W., Brozik, S. M., 2004. Biosens. Bioelectron. 19, 849-59.
Bronze, M. S., Huycke, M. M., Machado, L. J., Voskuhl, G. W., Greenfield, R. A., 2002. Am. J. Med. Sci. 323, 316-25.
Deisingh, A. K., Thompson, M., 2004. Can. J. Microbiol. 50, 69-77.
Frydenberg, A., Starr, M., 2003. Aust. Fam. Physician. 32, 594-5.
Hjelle, B., 2002. Expert Rev. Vaccines. 1, 373-84.
Jay, M., Ascher, M. S., Chomel, B. B., Madon, M., Sesline, D., Enge, B. A., Hjelle, B., Ksiazek, T. G., Rollin, P. E., Kass, P. H., Reilly, K., 1997. Emerg. Infect. Dis. 3, 183-90.
Martin, F., Newton, M. I., McHale, G., Melzak, K. A., Gizeli, E., 2004. Biosens. Bioelectron. 19, 627-32.
Mertz, G. J., Hjelle, B., Crowley, M., Iwamoto, G., Tomicic, V., Vial, P. A., 2006. Curr. Opin. Infect. Dis. 19, 437-42.
Moll, N., Pascal, E., Dinh, D. H., Pillot, J. P., Bennetau, B., Rebiere, D., Moynet, D., Mas, Y., Mossalayi, D., Pistré, J., Déjous C., 2007. Biosens. Bioelectron. 22, 2145-50.
Palacios, G., Oberste, M. S., 2005. J. Neurovirol. 11, 424-33.
Tam, P. E., 2006. Viral Immunol. 19, 133-46.
Tamarin, O., Comeau, S., Dejous, C., Moynet, D., Rebiere, D., Bezian, J., Pistre, J., 2003. Biosens. Bioelectron. 18, 755-63.
Tassew, N., Thompson, M., 2003. Org. Biomol. Chem. 1, 3268-70.
Velappan, N., Martinez, J. S., Valero, R., Chasteen, L., Ponce, L., Bondu-Hawkins, V., Kelly, C., Pavlik, P., Hjelle, B., Bradbury, A. R., 2007. J. Immunol. Methods. 321, 60-9.
Xiao, R., Yang, S., Koster, F., Ye, C., Stidley, C., Hjelle, B., 2006. J. Infect. Dis. 194, 1403-.

The invention claimed is:

1. A method of identifying the presence of a bioagent or analyte in a sample with a ligand based biosensor comprising a biological ligand complexed, directly or indirectly to a surface of a lithium tantalite (LiTaO$_3$) piezoelectric material which is coated with a thin layer of silicon dioxide, said ligand being capable of binding said bioagent or analyte, said piezoelectric material being operably connected to an electric circuit and being capable of producing high frequency shear-horizontal surface acoustic waves on the surface of the piezoelectric material to detect the binding of said bioagent or analyte to said ligand on said biosensor, said method comprising establishing high frequency shear-horizontal surface acoustic waves on the surface of said piezoelectric material comprising said ligand which is capable of binding to said bioagent or analyte, exposing said surface to a sample suspected of containing said bioagent or analyte and then determining whether the sample contains a suspect bioagent or analyte if the shear horizontal surface acoustic waves at the surface of said piezoelectric material evidence a change consistent with the binding of said bioactive or analyte agent to said ligand, wherein said bioagent or analyte is selected from the group consisting of viruses and virus extracts, prions and prion extracts, eucaryotic cells, fragments and extracts, prokaryotic cells, fragments and extracts, prokaryotic spores, fragments and extracts, protein and peptide markers, serum proteins, isolated proteins, polypeptides, synthetic chemicals, viral membranes, eukaryotic membranes, eukaryotic cell parts, including mitochondria and other organelles, prokaryotic membranes, DNA viruses, RNA viruses, point mutations, single nucleotide polymorphism, mRNA's, rTNAs or a micro RNA, said ligand is an antibody, and wherein said high frequency shear-horizontal surface acoustic waves have an input frequency ranging from about 275 to 400 Mhz.

2. The method according to claim 1 wherein said sample is an environmental or human sample.

3. The method according to claim 2 wherein said human sample is blood, serum, plasma, urine, sputum or fecal matter.

4. The method according to claim 1 wherein said surface acoustic wave has an input frequency ranging from 315 to about 400 Mhz.

5. The method according to claim 1 wherein said surface acoustic wave has an input frequency ranging from 315-330 MHz.

6. The method according to claim 1 wherein said surface acoustic wave has an input frequency of about 325 Mhz.

7. The method according to claim 1 wherein said ligand is covalently or non-covalently linked to said silicone dioxide layer on said piezoelectric material, said silicon dioxide layer ranging in thickness from about 500 Å to about 10,000 Å and being produced on the surface of said piezoelectric material using plasma enhanced chemical vapor deposition (PECVD).

8. The method according to claim 7 wherein said silicon dioxide layer is about 5000 Å thick.

9. The method according to 82 wherein hexamethyldisilazane is added to said silicone dioxide layer wherein said ligand is physisorbed to said hexamethyldisilazane.

10. The method according to claim 1 wherein said antibody is a polyclonal antibody.

11. The method according to claim 1 wherein said antibody is a monoclonal antibody.

12. The method according to claim 1 wherein said change is evidenced by a change in the phase of the acoustic waves when said analyte binds to said antibody.

13. The method according to claim 1 wherein said prokaryotic cells are bacteria.

14. The method according to claim 1 wherein said prokaryotic fragments, extracts and membranes are of bacterial origin.

15. The method according to claim 1 wherein said analyte is a prion or prion extract.

* * * * *

SEQUENCE LISTING

<160> NUMBER OF SEQ ID NOS: 36

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Cys Leu Val Arg Asn Leu Ala Trp Cys
1               5

```
<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Cys Ser Ala Ser Thr Glu Ser Leu Cys
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Cys Gln Thr Thr Asn Trp Asn Thr Cys
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Cys Lys Ser Phe Thr Thr Thr Arg Cys
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptide

<400> SEQUENCE: 5

Cys Ala Glu Pro Asn Ser His Arg Cys
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic peptide

<400> SEQUENCE: 6

Cys Lys Gln Thr Thr Asn Arg Asn Cys
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Cys Gln Ala Thr Thr Ala Arg Asn Cys
1               5

<210> SEQ ID NO 8
```

```
<211> LENGTH: 9
<212> TYPE: PRT
<213> ORGANISM: Artificial Sequence
<220> FEATURE:
<223> OTHER INFORMATION: synthetic peptide

<400> SEQUENCE: 8

Cys Ser Ala Gly Ala Pro Glu Phe Cys
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic peptide

<400> SEQUENCE: 9

Cys Thr Gln Ser Gly Leu Leu Ser Cys
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic peptide

<400> SEQUENCE: 10

Cys Lys Ser Phe Thr Thr Thr Arg Cys
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic peptide

<400> SEQUENCE: 11

Cys Thr Tyr Pro Tyr Pro Lys Phe Cys
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic peptide

<400> SEQUENCE: 12

Cys Lys Ser Thr Phe Ser Pro Asn Cys
1               5

<210> SEQ ID NO 13
<211> LENGTH: 9
<212> TYPE: PRT
<213> ORGANISM: Artificial Sequence
<220> FEATURE:
<223> OTHER INFORMATION: synthetic peptide

<400> SEQUENCE: 13

Cys Thr Ser Ala Ala Val His Met Cys
1               5

<210> SEQ ID NO 14
<211> LENGTH: 9
```

```
<212> TYPE: PRT
<213> ORGANISM: Artificial Sequence
<220> FEATURE:
<223> OTHER INFORMATION: synthetic peptide

<400> SEQUENCE: 14

Cys Gln Pro His Leu Pro Trp His Cys
1               5

<210> SEQ ID NO 15
<211> LENGTH: 9
<212> TYPE: PRT
<213> ORGANISM: Artificial Sequence
<220> FEATURE:
<223> OTHER INFORMATION: synthetic peptide

<400> SEQUENCE: 15

Cys Gln Trp Pro Gly Gln Ser Gly Cys
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic peptide

<400> SEQUENCE: 16

Cys Asn Ser Ser Ser Pro Thr Ala Cys
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic peptide

<400> SEQUENCE: 17

Cys His Gln Leu Met Gln Asn Leu Cys
1               5

<210> SEQ ID NO 18
<211> LENGTH: 8
<212> TYPE: PRT
<213> ORGANISM: Artificial Sequence
<220> FEATURE:
<223> OTHER INFORMATION: synthetic peptide

<400> SEQUENCE: 18

Cys Ile Gln Ser Gly Leu Leu Ser
1               5

<210> SEQ ID NO 19
<211> LENGTH: 9
<212> TYPE: PRT
<213> ORGANISM: Artificial Sequence
<220> FEATURE:
<223> OTHER INFORMATION: synthetic peptide

<400> SEQUENCE: 19

Cys Pro Lys Leu His Pro Gly Gly Cys
1               5

<210> SEQ ID NO 20
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 20

Cys Pro Met Ser Gln Asn Pro Thr Cys
1               5

<210> SEQ ID NO 21
<211> LENGTH: 9
<212> TYPE: PRT
<213> ORGANISM: Artificial Sequence
<220> FEATURE:
<223> OTHER INFORMATION: synthetic peptide

<400> SEQUENCE: 21

Cys Thr Val Gly Pro Thr Arg Ser Cys
1               5

<210> SEQ ID NO 22
<211> LENGTH: 9
<212> TYPE: PRT
<213> ORGANISM: Artificial Sequence
<220> FEATURE:
<223> OTHER INFORMATION: synthetic peptide

<400> SEQUENCE: 22

Cys Pro Ser Asn Val Asn Asn Ile Cys
1               5

<210> SEQ ID NO 23
<211> LENGTH: 9
<212> TYPE: PRT
<213> ORGANISM: Artificial Sequence
<220> FEATURE:
<223> OTHER INFORMATION: synthetic peptide

<400> SEQUENCE: 23

Cys Met Gln Ser Ala Ala Ala His Cys
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic peptide

<400> SEQUENCE: 24

Cys Asn Ser His Ser Pro Val His Cys
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic peptide

<400> SEQUENCE: 25

Cys Lys Ser Leu Gly Ser Ser Gln Cys
1               5

<210> SEQ ID NO 26
<211> LENGTH: 9
<212> TYPE: PRT
<213> ORGANISM: Artificial Sequence
```

```
<220> FEATURE:
<223> OTHER INFORMATION: synthetic peptide

<400> SEQUENCE: 26

Cys Pro Ala Ala Ser His Pro Arg Cys
1               5

<210> SEQ ID NO 27
<211> LENGTH: 9
<212> TYPE: PRT
<213> ORGANISM: Artificial Sequence
<220> FEATURE:
<223> OTHER INFORMATION: synthetic peptide

<400> SEQUENCE: 27

Cys Glu Lys Leu His Thr Ala Ser Cys
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic peptide

<400> SEQUENCE: 28

Cys Ser Leu His Ser His Lys Gly Cys
1               5

<210> SEQ ID NO 29
<211> LENGTH: 16
<212> TYPE: PRT
<213> ORGANISM: Artificial Sequence
<220> FEATURE:
<223> OTHER INFORMATION: synthetic peptide

<400> SEQUENCE: 29

Asp Thr Arg Ala Cys Asp Val Ile Ala Leu Leu Cys His Leu Asn Thr
1               5                   10                  15

<210> SEQ ID NO 30
<211> LENGTH: 27
<212> TYPE: DNA
<213> ORGANISM: Sin Nombre hantavirus

<400> SEQUENCE: 30
ccctagagat gctgcattgg caactaa                                             27

<210> SEQ ID NO 31
<211> LENGTH: 27
<212> TYPE: DNA
<213> ORGANISM: Sin Nombre hantavirus

<400> SEQUENCE: 31
ttacaggttg atgagtcaaa agttagt                                             27

<210> SEQ ID NO 32
<211> LENGTH: 40
<212> TYPE: DNA
<213> ORGANISM: Sin Nombre hantavirus

<400> SEQUENCE: 32
ttacaggttg atgagtcaaa agttagtgat attgaggacc                               40

<210> SEQ ID NO 33
```

```
<211> LENGTH: 40
<212> TYPE: DNA
<213> ORGANISM: Sin Nombre hantavirus

<400> SEQUENCE: 33
cctgatcaaa atggacaagg tttaatgaga atagctgggc                          40

<210> SEQ ID NO 34
<211> LENGTH: 27
<212> TYPE: DNA
<213> ORGANISM: Sin Nombre hantavirus

<400> SEQUENCE: 34
tttcatgctc acattattct acagaat                                        27

<210> SEQ ID NO 35
<211> LENGTH: 40
<212> TYPE: DNA
<213> ORGANISM: Sin Nombre hantavirus

<400> SEQUENCE: 35
tttcatgctc acattattct acagaatcaa aattcaaagt                          40

<210> SEQ ID NO 36
<211> LENGTH: 30
<212> TYPE: DNA
<213> ORGANISM: Sin Nombre hantavirus

<400> SEQUENCE: 36
cctggataat gggtttatga aaaacacttt                                     30
```